(12) United States Patent
Kevil et al.

(10) Patent No.: US 10,864,229 B2
(45) Date of Patent: *Dec. 15, 2020

(54) USE OF NITRITE SALTS IN CHRONIC ISCHEMIA

(71) Applicants: The UAB Research Foundation, Birmingham, AL (US); The Board of Supervisors of Louisiana State University and Agricultural and Mechanical College, Baton Rouge, LA (US)

(72) Inventors: Christopher Kevil, Shreveport, LA (US); David Lefer, Decatur, GA (US); Rakesh Patel, Hoover, AL (US)

(73) Assignee: BOARD OF SUPERVISORS OF LOUISIANA STATE UNIVERSITY, Baton Rouge, LA (US)

( * ) Notice: Subject to any disclaimer, the term of this patent is extended or adjusted under 35 U.S.C. 154(b) by 1 day.

This patent is subject to a terminal disclaimer.

(21) Appl. No.: 15/483,187

(22) Filed: Apr. 10, 2017

(65) Prior Publication Data

US 2017/0312310 A1 Nov. 2, 2017

Related U.S. Application Data

(63) Continuation of application No. 12/741,436, filed as application No. PCT/US2008/083830 on Nov. 17, 2008, now Pat. No. 9,649,334.

(60) Provisional application No. 61/003,150, filed on Nov. 15, 2007.

(51) Int. Cl.
| A61K 33/06 | (2006.01) |
| A61K 33/00 | (2006.01) |
| A61K 45/06 | (2006.01) |
| A61P 25/02 | (2006.01) |

(52) U.S. Cl.
CPC .............. *A61K 33/06* (2013.01); *A61K 33/00* (2013.01); *A61K 45/06* (2013.01); *A61P 25/02* (2018.01)

(58) Field of Classification Search
CPC ....... A61K 9/0053; A61K 33/00; A61P 25/02; C01B 21/50
See application file for complete search history.

(56) References Cited

U.S. PATENT DOCUMENTS

| 2,914,446 | A | 11/1959 | MacDonald et al. |
| 4,650,484 | A | 3/1987 | Shaw et al. |
| 5,122,384 | A | 6/1992 | Paradissis et al. |
| 5,489,610 | A | 2/1996 | Fung et al. |
| 5,648,101 | A | 7/1997 | Tawashi |
| 5,770,645 | A | 6/1998 | Stamler et al. |
| 5,994,444 | A | 11/1999 | Trescony et al. |
| 6,103,275 | A | 8/2000 | Seitz et al. |
| 6,641,839 | B1 | 11/2003 | Geoghegan et al. |
| 6,709,681 | B2 | 3/2004 | Benjamin et al. |
| 6,962,717 | B1 | 11/2005 | Huber et al. |
| 7,371,415 | B1 | 5/2008 | Wuh et al. |
| 8,568,793 | B2 | 10/2013 | Sherman et al. |
| 9,561,249 | B2* | 2/2017 | Kevil ..................... A61K 45/06 |
| 9,649,334 | B2* | 5/2017 | Kevil ..................... A61K 33/00 |
| 10,307,441 | B2* | 6/2019 | Kevil ..................... A61K 33/00 |
| 2003/0125714 | A1 | 7/2003 | Edgren et al. |
| 2003/0219495 | A1 | 11/2003 | Juneau et al. |
| 2004/0006140 | A1 | 1/2004 | Kaesemeyer |
| 2005/0113409 | A1 | 5/2005 | Connor et al. |
| 2006/0083824 | A1 | 4/2006 | Manning et al. |
| 2006/0125714 | A1 | 6/2006 | Miller |
| 2006/0182815 | A1 | 8/2006 | Gladwin et al. |
| 2007/0010571 | A1 | 1/2007 | Garvey et al. |
| 2007/0154569 | A1* | 7/2007 | Gladwin ................ A61K 33/00 424/718 |
| 2007/0190209 | A1 | 8/2007 | Sinnott |
| 2009/0196930 | A1 | 8/2009 | Surber et al. |
| 2009/0297634 | A1 | 12/2009 | Friedman et al. |
| 2010/0092441 | A1* | 4/2010 | Lundberg ............... A61K 31/05 424/93.45 |
| 2010/0247682 | A1 | 9/2010 | Gladwin et al. |

(Continued)

FOREIGN PATENT DOCUMENTS

| EP | 1 336 602 A1 | 8/2003 |
| WO | WO-1994/01103 A1 | 1/1994 |

(Continued)

OTHER PUBLICATIONS

Namba et al (Angiogenesis Induced by Endothelial Nitric Oxide Synthase Gene Through Vascular Endothelial Growth Factor Expression in a Rat Hindlimb Ischemia Model, Oct. 20, 2003 online, Circulation, vol. 108, pp. 2250-2257) (Year: 2003).*

(Continued)

*Primary Examiner* — Mark V Stevens
(74) *Attorney, Agent, or Firm* — Davis & Bujold PLLC; Michael J. Bujold; Charles G. Holoubek

(57) ABSTRACT

Methods of treating a subject who has chronic tissue ischemia are disclosed. The methods can include administering to the subject a pharmaceutical composition comprising inorganic nitrite or a pharmaceutically acceptable salt thereof, for a time and in an amount sufficient to result in blood vessel growth in the ischemic tissue. The subject can be diagnosed as having a medical condition that results in persistent or recurring restriction of blood supply to a tissue, for example, peripheral artery disease, diabetes, atherosclerotic cardiovascular disease or defective wound healing. The methods can include the step of identifying a suitable subject.

8 Claims, 13 Drawing Sheets

(56) References Cited

U.S. PATENT DOCUMENTS

| | | | |
|---|---|---|---|
| 2011/0086069 A1 | 4/2011 | Kevil et al. | |
| 2011/0311653 A1 | 12/2011 | Kevil et al. | |
| 2012/0237617 A1 | 9/2012 | Kevil | |
| 2013/0170357 A1 | 7/2013 | Anchan et al. | |
| 2013/0209584 A1 | 8/2013 | Kevil et al. | |

FOREIGN PATENT DOCUMENTS

| | | | | |
|---|---|---|---|---|
| WO | WO-00-003725 A1 | 1/2000 | | |
| WO | WO-00-053193 A1 | 9/2000 | | |
| WO | WO-01-17596 A1 | 3/2001 | | |
| WO | WO-03-013489 A1 | 2/2003 | | |
| WO | WO-2005-004884 A2 | 1/2005 | | |
| WO | WO-2005/007173 A1 | 1/2005 | | |
| WO | WO-2005004884 A2 * | 1/2005 | ............ | A61K 33/00 |
| WO | WO-2006-128032 A2 | 11/2006 | | |
| WO | WO-2007/116102 A2 | 10/2007 | | |
| WO | WO-2008/105730 A1 | 9/2008 | | |
| WO | WO-2008/105731 A1 | 9/2008 | | |
| WO | WO-2008/153762 A2 | 12/2008 | | |
| WO | WO-2009-065142 A2 | 5/2009 | | |
| WO | WO-2010-036236 A1 | 4/2010 | | |
| WO | WO-2010-147742 A2 | 12/2010 | | |
| WO | WO-2011-047161 A1 | 4/2011 | | |
| WO | WO-2012-135623 A1 | 10/2012 | | |
| WO | WO-2012-142413 A2 | 10/2012 | | |

OTHER PUBLICATIONS

Hord et al (American Journal of Clinical Nutrition, 2009, vol. 90, pp. 1-10) (Year: 2009).*

"In High Blood Pressure," The Canadian Medical Association Journal p. xliii, 1928.

"Peripheral arterial disease in people with diabetes," Diabetes Care 23(12):3333-3341 (2003).

Allen et al., "Plasma Nitrite Response and Arterial Reactivity Differentiate Vascular Health and Performance," Nitric Oxide, 20:231-237 (2009).

Blood et al., "In Vitro and in vivo kinetic handling of nitrite in blood: Effects of varying hemoglobin exygen saturation," Am J Physiol Heart Circ Physiol. 293:H1508-H1517 (2007).

Bondonno et al., "Short-term effects of a high nitrate diet on nitrate metabolism in healthy individuals," Nutrients, 7(3):1906-15 (2015).

Bryan et al., "Dietary nitrite supplementation protects against myocardial ischemia-repurfusion injury," Proc Natl Acad Sci USA 104(48):19144-19149 (2007).

Chiryougaku (Therapeutics) 24(8):926-927.

Colorcon, Opadry Enteric Application Data, accessed at https://www.colorcon.com Nov. 3, 2016 (Jan. 2009).

Combet et al, "Diet, gastric nitrosation and stomach cancer," Comparative Biochemistry and Physiology, Part A 146:S61 (2007) (Abstract only).

Contreras, et al. "The role of nitric oxide in the post-ischemic revascularization process," Pharmacol Ther. 112(2):553-63 (2006).

Cooke et al., "Nitric Oxide and Angiogenesis," Circulation, 105:2133-2135 (2002).

Cosby et al., "Nitrite reduction to nitric oxide by deoxyhemoglobin vasodilates the human circulation," NatMed. 9(12): 1498-1505 (2003).

Croft et al., "Ultrastructural studies of wound healing in mouse skin," J Anat 106:63-77 (1970).

Dejam et al., "Nitrite Infusion in Humans and Nonhuman Primates: Endocrine Effects, Pharmacokinetics, and Tolerance Formation," Circulation, 116:1821-1831 (2007).

Duncan et al., "Chemical generation of nitric oxide in the mouth from the enterosalivary circulation of dietary nitrate," Nat. Med., 1:546-551 (1995).

Duranski et al., "Cytoprotective effects of nitrite during in vivo ischemia-reperfusion of the heart and liver," J Clin Invest. 115(5):1232-1240 (2005).

Green et al., "Analysis of nitrate, nitrite and [15N]nitrate in biological fluids," Anal Biocehm., 126:131-138 (1982).

Greenberg, et al., "Nitro containing L-arginine analogs interfere with assays for nitrate and nitrite," Life Sci. 57(21):1949-61 (1995).

Greenway et al., "single-dose pharmacokinetics of different oral sodium nitrite formulations in diabetes patients," Diabetes Technol Ther. 14(7):552-560 (2012).

Grosse et al., "Carcinogenicity of nitrate, nitrite, and cyanobacterial peptide toxins," Lancet Oncology 7:628-629 (2006).

Hunault et al., "Bioavailability of Sodium Nitrite from an Aqueous Solution in Healthy Adults," Toxicology Letters, 190(1 ):48-53 (2009).

Jacoby et al., "Acute myocardial infarction in the diabetic patient: Pathophysiology, clinical course and prognosis," J Am Coll Cardiol 20(3):736-44 (1992).

Jadeski, "Nitric oxide synthase inhibition by N(G)-nitro-L-arginine methyl ester inhibits tumor induced angiogenesis in mammary tumors," Am J Pathol. 155(4):1381-90 (1999).

Jung et al., "Early Intravenous Infusion of Sodim Nitrite Protects Brain Against In Vivo Ischemia-Reperfusion Injury," Stroke 37:2744-2750 (2006).

Kenjale et al., "Dietary nitrate supplementation enhances exercise performance in peripheral arterial disease," J Appl. Physiol. 110:1592-1591 (2011).

Kevil, et al. "Inorganic nitrite therapy: historical perspective and future directions," Free Radic Biol Med. 51 (3):576-93 (2011).

Kohn et al., "Pharmacokinetics of Sodium Nitrite-Induced Methemoglobinemia in the Rat," *Drug Metabolism and Disposition*, 30(6):676-683 (2002).

Kumar et al., "Chronic Sodium Nitrite Therapy Augments Ischemia-Induced Angiogenesis and Arteriogenesis," *PNAS*, 105(21):7540-7545 (2008).

Kumar et al., "Nitrite enhances ischemia-induced angiogenesis by Nitric Oxide dependant pathway," FASEB Journal, Apr. 2007, Meeting abstract.

Mazzone et al., "A Lifeline for Suffocating Tissues," Nature, 453:1194-1195 (2008).

Medin et al., "Nitrite-Derived Nitric Oxide: A Possible Mediator of 'Acidic-Metabolic' Vasodilation," Acta Physiol. Scand. 171 :9-16 (2001 ).

Moshage et al., "Nitrite and nitrate determinations in plasma: a critical evaluation," Clin Chem. 41(6): 892-896, 1995.

Namba et al., "Angiogenesis Induced by Endothelial Nitric Oxide Synthase Gene Through Vascular Endothelial Growth Factor Expression in a Rat Hindlimb Ischemia Model," Circulation 108: 2250-2257, 2003.

Notice of Judgment Case No. 4151. Adulteration and misbranding of Natrico tablets. *U.S.* v. *140 Bottles* p. 147 (1954), accessed at http://archive.nim.nih.gov/fdanj/handle/123456789/12581.

Notices of Judgment Case 2310, Adulteration and alleged misbranding of drug tablets. *U.S.* v. *Charles H. Dietz, Inc.* p. 47-48 (1949), accessed at http://archive.nim.nih.gov/fdanj/handle/123456789/11149.

Pluta et al., "Sodium Nitrite as a therapeutic agent for central nervous system diseases," Surgical Neurology, 66:5-10 (2006).

Presley et al., "Acute effect of a high nitrate diet on brain perfusion in older adults," Nitric Oxide 24(1): 34-42, 2011.

Rikitake, et al., "Involvement of endothelial nitric oxide in sphingosine-1-phosphate-induced angiogenesis," Arterioscler Thromb Vasc Biol. 22(1 ):1 08-14 (2002).

Sun et al., "Measurement of nitric oxide production in biological systems by using griess reaction assay," Sensors 3: 276-284, 2003.

Sun, "Induction of angiogenesis by heat shock protein 90 mediated by protein kinase Akt and endothelial nitric oxide synthase," Arterioscler Thromb Vasc Biol. 24(12):2238-44 (2004).

Tripathi et al., "Effect of superoxide dismutase and acified sodium nitrate on infarct size following ischemia and reperfusion in dogs," Indian J Physiol Pharmacol 41(3):248-56 (1997).

Tsuchiya et al., "Nitrite is an alternative source of NO in vivo," Am J Physiol Heart Circ Physiol 288:H2163-2170 (2005).

Van Velzen et al., "The Oral Bioavailability of Nitrate from Nitrate-Rich Vegetables in Humans," Toxicology Letters, 181:177-181 (2008).

(56) References Cited

OTHER PUBLICATIONS

Verma, et al., "A self-fulfilling prophecy: C-reactive protein attenuates nitric oxide production and inhibits angiogenesis," Circulation. 106(8):913-9 (2002).
Vitecek, et al., "Arginine-based inhibitors of nitric oxide synthase: therapeutic potential and challenges" Mediators Inflamm. 2012(318087):1-22 (2012).
Wagner et al., "Metabolic Fate of an Oral Dose of 15N-labeled Nitrate in Humans: Effect of Diet Supplementation with Ascorbic Acid," Cancer Res. 43:1921-1925 (1983).
Weller et al., "The effects of topical treatment with acidified nitrite on wound healing in normal and diabetic mice," Nitric Oxide, 15(4):395-359 (2006).
Zhang et al., "Nitric Oxide Enhances Angiogenesis via Synthesis of Vascular Endothelial Growth Factor and cGMP After Stroke in the Rat," Circulation Research, 2003 92:308-313.
Ziche et al., "Nitric Oxide Mediates Angiogenesis In Vivo and Endothelial Cell Growth and Migration In Vitro Promoted by Substance P," J. Clin. Invest., 94:2036-2044, (1994).
Kleinbongard et al., Free Radical Biology & Medicine, 40: 395-302 (2006).
International Search Report and Written Opinion of the International Searching Authority for International Application No. PCT/US2010/052683, dated Dec. 13, 2010.
American Diabetes Association (Diabetes Care, 2003, vol. 26, pp. 3333-3341).
Supplementary European Search Report issued in corresponding European Patent Application No. 08849380.4 dated Dec. 9, 2019.

* cited by examiner

Chronic sodium nitrite therapy restores ischemic hind limb blood flow in an NO-dependent manner Fig. S1. Nonischemic hind-limb blood flow in response to PBS or sodium nitrite injection. *A* illustrates non-ischemic hind limb blood flow in response to i.p. injection of PBS. *B* shows nonischemic hind-limb blood flow in response to i.p. injection of 165 μg/kg sodium nitrite. n = 8 mice per treatment group.

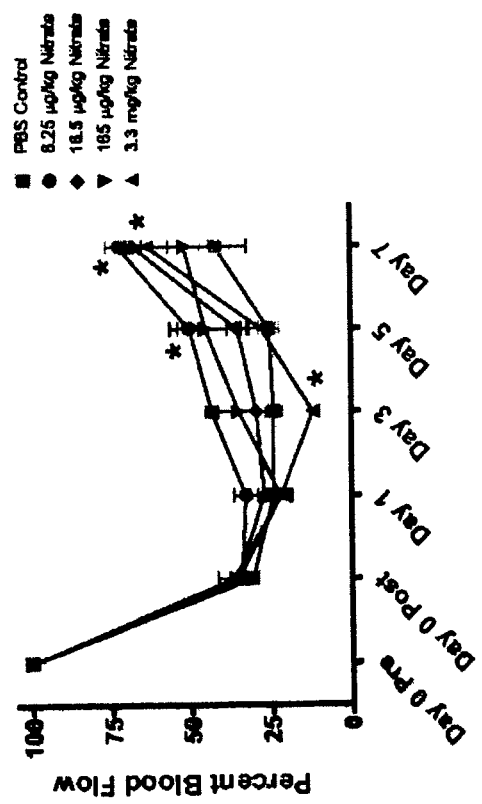

Chronic sodium nitrite therapy increases ischemic tissue vascular density in an NO-dependent manner

A

B

C

D

E

F

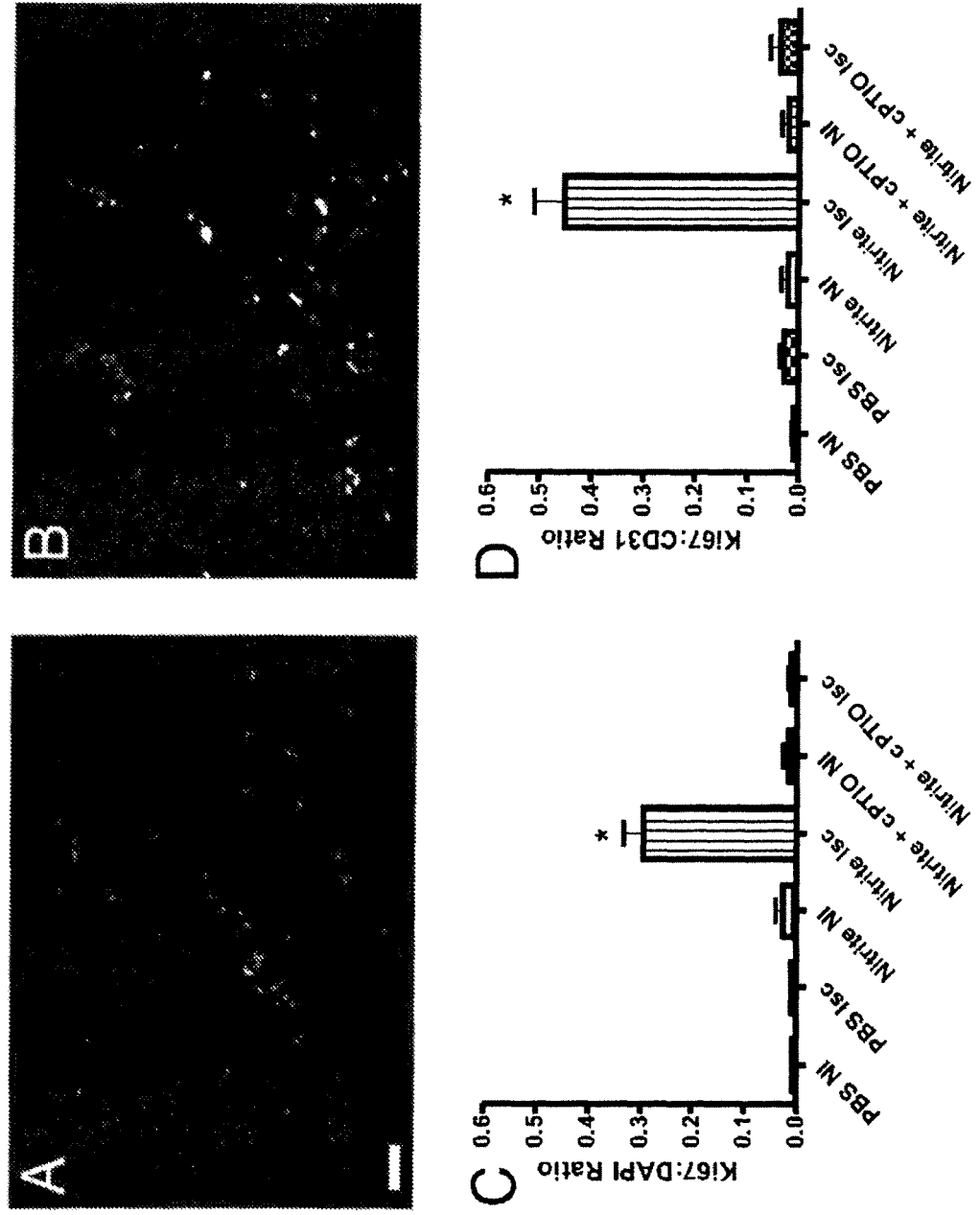

Chronic sodium nitrite therapy alters blood and tissue nitrite levels

Chronic sodium nitrite therapy effects on tissue NO metabolites and cGMP levels

Chronic sodium nitrite therapy acutely increases ischemic tissue blood flow and stimulates arteriogenesis Single Bolus I.P. Injection of Sodium Nitrite Does Not Restore Ischemic Hind-Limb Blood Flow Continuous Nitrite Therapy Enhances Wound Healing Sodium Nitrite Restores Db/Db Diabetic Mouse Ischemic Hind-Limb Blood Flow

USE OF NITRITE SALTS IN CHRONIC ISCHEMIA

CROSS-REFERENCE TO RELATED APPLICATIONS

This application is a continuation of U.S. patent application Ser. No. 12/741,436 filed Aug. 8, 2011, which is the U.S. National Stage of International Patent Application No. PCT/US2008/083830, filed Nov. 17, 2008, which claims the benefit of priority to U.S. Provisional Application No. 61/003,150, filed on Nov. 15, 2007, the entire contents of each of which are hereby incorporated by reference in their entirety.

FEDERALLY SPONSORED RESEARCH OR DEVELOPMENT

The work described below was support by Grant No. HL080482, which was awarded by the National Institutes of Health. The Government has certain rights in the invention.

TECHNICAL FIELD

This invention relates to methods and compositions useful for the treatment of chronic tissue ischemia, and more particularly to methods for inducing new blood vessel growth in ischemic tissue.

BACKGROUND

Chronic tissue ischemia, i.e., persistent restriction of blood supply to a tissue, can impair tissue function and result in tissue and organ damage. Chronic tissue ischemia in critical organ systems or body parts, for example, heart, brain, kidneys, skin, limbs, or gastrointestinal tract, contributes significantly to human morbidity and mortality and there is a continuing need for therapeutic strategies that restore blood supply to affected regions.

SUMMARY

The present invention is based, in part, on our discovery of compositions and methods that can be used to treat chronic tissue ischemia, including chronic tissue ischemia associated with a disorder, trauma or a congenital defect. The chronic tissue ischemia encompassed by the methods of the invention can stem from any of a wide range of medical conditions that result in the persistent or recurring restriction of blood supply to the tissue, for example, disorders such as peripheral artery disease, type 1 or type 2 diabetes, atherosclerotic cardiovascular disease, intermittent claudication (which can manifest as cramping pain in the extremities due to inadequate blood supply), critical limb ischemic disease, stroke, myocardial infarction, inflammatory bowel disease, and peripheral neuropathy; traumatic injuries such as wounds, burns, lacerations, contusions, hone fractures, infections, or surgical procedures; congenital malformations such as hernias, cardiac defects and gastrointestinal defects. Thus, chronic tissue ischemia can occur in a variety of tissue types including, for example, skeletal muscle, smooth muscle, cardiac muscle, neuronal tissue, skin, mesenchymal tissue, connective tissue, gastrointestinal tissue and bone.

Regardless of whether the methods are described with respect to a particular medical condition or tissue type, the methods can be carried out by administering to a subject (e.g., a human patient) in need of treatment a pharmaceutically acceptable composition comprising inorganic nitrite or a pharmaceutically acceptable salt thereof. The inorganic nitrite or a pharmaceutically acceptable salt thereof can be formulated in various ways and can include pharmaceutically acceptable carriers. For ease of reading, we will not repeat the phrase "or a pharmaceutically acceptable salt thereof" on every occasion. It is to be understood that where inorganic nitrite can be used, a pharmaceutically acceptable salt of the compound may also be used.

Accordingly, the invention features physiologically acceptable compositions of inorganic nitrite and methods by which the compositions can be administered to a patient diagnosed as having, for example, a chronic tissue ischemic disorder. These methods can include the steps of a) identifying a subject (e.g., a human patient) who is experiencing or is likely to experience a chronic tissue ischemic disorder; and b) providing to the subject a composition including inorganic nitrite for a time and in an amount sufficient to stimulate blood vessel growth in the ischemic tissue. The nitrite can result in the formation of a blood vessel that did not exist prior to treatment or in an increase in the size of existing vessels. The increase in size is due to formation of new tissue (e.g., new tissue added to the vessel wall); it is not the result of simple vasodilation. Patients amenable to being treated with inorganic nitrite can also be treated with nitrate. We may use the terms "subject," "individual" and "patient" interchangeably. While the present methods are certainly intended for application to human patients, the invention is not so limited. Domesticated animals, including, for example cats, dogs, horses, cows and other domesticated animals can also be treated.

The pharmaceutically acceptable compositions of the invention include inorganic nitrite, e.g., a salt or ester of nitrous acid ($HNO_2$) or a pharmaceutically acceptable salt thereof. As used herein, "pharmaceutically acceptable salts" refers to derivatives of the disclosed compounds wherein the parent compound is modified by converting an existing acid or base moiety to its salt form. Examples of pharmaceutically acceptable salts include, but arc not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred.

Suitable pharmaceutically acceptable salts can include, for example, sodium nitrite, potassium nitrite, or calcium nitrite. The invention is not so limited however and lists of exemplary salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety. It will also be understood that certain nitrite compounds of the present invention may exist in solvated, for example hydrated, as well as unsolvated forms. Nitrite has the chemical formula $NO_2{-}$ and may exist as an ion in water. Sodium nitrite has the chemical formula $NaNO_2$ and typically dissolves in water to form the sodium ion Na+ and the nitrite ion $NO_2$. It will further be understood that the present invention encompasses all such solvated forms of the nitrite compounds.

The inorganic nitrite is administered for a time and in an amount sufficient to result in the growth of blood vessels in the ischemic tissue. The new blood vessel growth may stem from any process that results in revascularization of the ischemic tissue, for example, angiogenesis, i.e., the budding of new capillary branches from existing blood vessels, or arteriogenesis, i.e., the growth of preexisting arteriolar connections into true collateral arteries, or a combination of angiogenesis and arteriogenesis. New blood vessel grow may be monitored over the course of treatment either directly, using, for example imaging techniques such as contrast angiography, contrast pulse sequence (CPS) ultrasound imaging for high-resolution perfusion, biomarkers, or indirectly, i.e., by monitoring a clinical endpoint. For example, the nitrite may be administered until a symptom of chronic ischemia, e.g., intermittent claudication, claudication during rest, neuropathy, or defective tissue wound healing, improves. The assessment of clinical benefit may entail comparison of the ischemic tissue with the corresponding non-ischemic tissue. Choice of specific clinical endpoints may depend, in part, upon the nature of the underlying medical condition, e.g., cessation or amelioration of intermittent claudication may be useful for patients with peripheral artery disease or diabetes; healing of skin ulcers may be useful for patients with defective wound healing, and relief from gastrointestinal pain, diarrhea and constipation may be useful for patient suffering from bowel ischemia.

The amount of inorganic nitrite per dose can vary. For example, a subject can receive from about 0.05 µg/kg up to about 5000 µg/kg., e.g., about 0.05, 1, 5, 10, 25, 50, 100, 200, 250, 300, 400, 450, 500, 550, 600, 650, 700, 750, 800, 850, 900, 1000, 1250, 1500, 2000, 2500, 3000, 3500, 4000, 4500 or 5000 µg/kg. For example, a subject can receive up to or up to about 165 µg/kg, 16.5 µg/kg, or 8.25 µg/kg. Generally, we administer nitrite in an amount such that the circulating concentration does not exceed 0.6 µM (i.e., the nitrite is administered in a dose sufficient to produce a circulating concentration of nitrite in the subject that does not exceed 0.6 µM). For example, the nitrite can be administered in an amount such that the circulating concentration does not exceed 0.0005 µM, 0.001 µM, 0.002 µM, 0.003 µM, 0.004 µM, 0.005 µM, 0.01 µM, 0.02 µM, 0.03 µM, 0.04 µM, 0.05 µM, 0.1 µM, 0.15 µM, 0.2 µM, 0.25 µM, 0.3 µM, 0.35 µM, 0.4 µM, 0.45 µM, 0.5 µM, 0.55 µM or 0.6 µM. Thus, exemplary dosages can produce a circulating concentration of nitrite in the subject of up to or up to about 0.03 µM, 0.003 µM, or 0.0015 µM.

The frequency of treatment may also vary. The subject can be treated one or more times per day (e.g., once, twice, three, four, five, or six times per day) or every so-many hours (e.g., about every 2, 4, 6, 8, 12, or 24 hours). The time course of treatment may be of varying duration, e.g., for two, three, four, five, six, seven, eight, nine, ten or more days. For example, the treatment can be twice a day for three days, twice a day for seven days, twice a day for ten days. Treatment cycles can be repeated at intervals, for example weekly, bimonthly or monthly, which are separated by periods in which no treatment is given. The treatment can be a single treatment or can last as long as the life span of the subject (e.g., many years).

The compositions can be administered to a subject in a variety of ways. For example, the compositions can he administered transdermally or injected (infused) intravenously, subcutaneously, sublingually, intracranially, intramuscularly, intraperitoneally, or intrapulmonarily. Oral formulations arc also within the scope of the present invention. The treatment regime can vary depending upon various factors typically considered by one of ordinary skill in the art. These factors include the route of administration, the nature of the formulation, the nature of the patient's illness, the subject's size, weight, surface area, age, gender, other drugs being administered to the patient, and the judgment of the attending physician. The compositions can be administered along with or in addition to other treatments for chronic tissue ischemia, e.g., drug therapy, immunotherapy, or surgery (e.g., aspirin therapy, statin therapy, or antihypertensive therapy).

Disorders amenable to the methods of the invention can include any disorder that presents with chronic ischemia. Conditions that result in chronic tissue ischemia due to a narrowing or blockage of an artery, for example, include but are not limited to, for example, atherosclerosis, arteriosclerosis, acute coronary syndrome, coronary artery disease (CAD), stroke, bowel ischemia and peripheral artery diseases. Also encompassed by the invention is chronic tissue ischemia that stems from a wound, e.g. a traumatic injury or a surgical procedure.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG 1A depicts the effect of various doses of chronic sodium nitrite therapy on ischemic hind-limb blood flow over time compared to PBS control. FIG. 1B depicts the effect of sodium nitrite therapy plus 1 mg/kg carboxy PTIO treatment on ischemic hind-limb blood flow. FIG. 1C depicts the effect of 165 µg/kg sodium nitrite injection on ischemic limb blood flow. FIG. 1D depicts the effect of PBS injection on ischemic limb blood flow. *, $P<0.01$ vs. PBS control at each time point; #, $P<0.01$ 165 µg/kg sodium nitrite vs. 165 µg/kg sodium nitrite plus cPTIO at each time point.

FIG. 2A shows non-ischemic hind-limb blood flow in response to intra-peritoneal injection of PBS. FIG. 2B depicts non-ischemic hind-limb blood flow in response to intra-peritoneal injection of 165 µg/kg sodium nitrite.

FIG. 3 depicts the results of an analysis of the effect of various doses of chronic sodium nitrate treatment on ischemic hind-limb blood flow.

FIGS. 4A and 4B depict representative images of CD31 (red) and DAPI nuclear (blue) staining ischemic gastrocnemius muscle tissue at day 7 from sodium nitrite-treated and sodium nitrate-treated animals, respectively. FIG. 4C and FIG. 4D depict the vascular density of ischemic gastrocnemius muscle tissue at days 3 and 7 for 165 µg/kg sodium nitrite and nitrate treatments, respectively. FIG. 4E and FIG. 4F depict the vascular density of ischemic gastrocnemius muscle tissue at days 3 and 7 from 165 µg/kg sodium nitrite plus carboxy PTIO. (Scale bar, 150 µm.).

FIGS. 5A and FIG. 5B depict the vascular density of ischemic gastrocnemius muscle tissue for 3.3 mg/kg sodium nitrite and nitrate treatments at days 3 and 7, respectively. FIG. 5C depicts the vascular density measurements at day 7 of non-ischemic gastrocnemius muscle tissue from PBS-control and 165 µg/kg sodium nitrite-treated mice and nitrate-treated mice. n=10 mice per treatment group.

FIGS. 6A, 6B, 6C and 6D depict the results of an experiment demonstrating that chronic sodium nitrite treatment stimulated endothelial cell proliferation in an NO-dependent manner. FIG. 6A and FIG. 6B depict representative images of Ki67 proliferation marker (green), CD31 (red), and DAPI nuclear (blue) staining from day 3 ischemic gastrocnemius muscle tissue from PBS and 165 µg/kg sodium nitrite-treated animals, respectively. FIG. 6C depicts the amount of Ki67 colocalization with DAPI nuclear staining between PBS and sodium nitrite-treated tissues±cPTIO. FIG. 6D depicts the measurement of Ki67 colocalization with CD31 staining between PBS and sodium nitrite-treated tissues plus cPTIO. *, $P<0.001$ sodium nitrite vs. PBS or nitrite plus PTIO. (Scale bar, 150 µm.)

FIG. 7A depicts blood nitrite levels at days 3 and 7 for PBS control and sodium nitrite (165 µg/kg). *, $P<0.01$ treatments vs. PBS control blood nitrite levels. FIG. 7B and FIG. 7C depict tissue nitrite levels for PBS-treated control and sodium nitrite-treated animals (165 µg/kg) at day 3 and 7, respectively. *, $P<0.01$ ischemic vs. nonischemic tissue nitrite levels. FIG. 7D and FIG. 7E depict total cNOS protein expression normalized to β actin expression for PBS-treated and sodium nitrite-treated animals at day 3 and 7, respectively in ischemic and nonischemic hind-limbs.

FIG. 8A and FIG. 8B depict the amount of SNO+XNO levels in nonischemic and ischemic tissues at day 3 and 7 for PBS control and 165 µg/kg sodium nitrite, respectively. FIG. 8C and FIG. 8D report the pg/mg total protein of cGMP in nonischemic and ischemic tissues at day 3 and 7 for PBS control and 165 µg/kg sodium nitrite, respectively.

FIG. 9A and FIG. 9B depict 165 µg/kg sodium nitrite-induced acute changes in blood flow of chronically ischemic tissues at various time points with or without cPTIO, respectively. FIG. 9C depict the number of arterial branches in PBS-treated control and sodium nitrite-treated animals. FIG. 9D and FIG. 9E depict vascular casting of the arterial vasculature in ischemic hind limbs of day 7 nitrite-treated and PBS-treated mice, respectively. *, $P<0.01$ vs. sodium nitrate.

Like reference symbols in the various drawings indicate like elements.

DETAILED DESCRIPTION

Figures 1A, 1B, 1C, 1D:
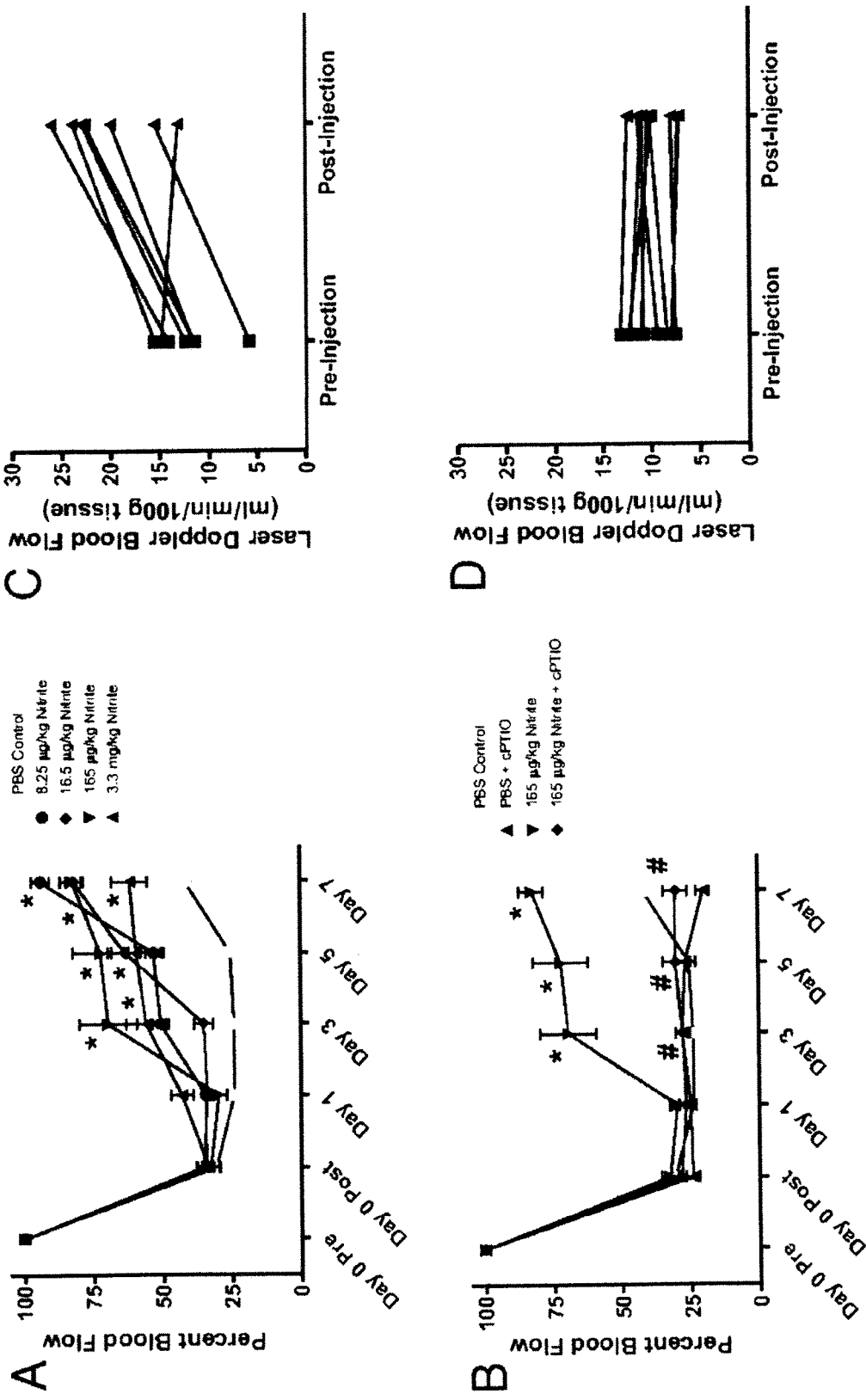
FIGS. 1A, 1B, 1C and 1D depict the results of an analysis demonstrating that chronic sodium nitrite treatment restored ischemic hind limb blood flow in an NO-dependent manner. effect of chronic sodium nitrite therapy on ischemic hind limb blood flow.

We further describe below the present methods for treatment of chronic tissue ischemia. These methods can be applied to, and are expected to benefit subjects having any of a variety of medical conditions that can give rise to chronic tissue ischemia. The methods are based, inter alia, on the inventor's discovery that administration of inorganic nitrite or a pharmaceutical composition comprising inorganic nitrite to a subject having chronic tissue ischemia results in the selective growth of new blood vessels in the ischemic tissue.

Compositions

The pharmaceutically acceptable compositions of the invention include inorganic nitrite, e.g., a salt or ester of nitrous acid ($HNO_2$) or a pharmaceutically acceptable salt thereof. The nitrite ion is NO2-. More generally, a nitrite compound is either a salt or an ester of nitrous acid. Nitrite salts can include, without limitation, salts of alkali metals, e.g., sodium, potassium; salts of alkaline earth metals, e.g., calcium, magnesium, and barium: and salts of organic bases, e.g., amine bases and inorganic bases. Compounds of the invention also include all isotopes of atoms occurring in the intermediate or final compounds. Isotopes include those atoms having the same atomic number but different mass numbers. For example, isotopes of hydrogen include tritium and deuterium. The term, "compound," as used herein with respect to any inorganic nitrite or pharmaceutically acceptable salt thereof and is meant to include all stereoisomers, geometric iosomers, tautomers, and isotopes of the structures depicted. All compounds, and pharmaceutically acceptable salts thereof, are also meant to include solvated or hydrated forms.

The compounds of the present invention can be prepared in a variety of ways known to one of ordinary skill in the art of chemical synthesis. The compounds of the present invention can be synthesized using the methods described below, together with synthetic methods known in the art of synthetic chemistry or variations thereon as appreciated by one of ordinary skill in the art. Methods for preparing nitrite salts are well known in the art and a wide range of precursors and nitrite salts are readily available commercially. Nitrites of the alkali and alkaline earth metals can be synthesized by reacting a mixture of nitrogen monoxide (NO) and nitrogen dioxide ($NO_2$) with a corresponding metal hydroxide solution, as well as through the thermal decomposition of the corresponding nitrate. Other nitrites are available through the reduction of the corresponding nitrates.

The present compounds can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one of ordinary skill in the art by routine optimization procedures.

Regardless of their original source or the manner in which they are obtained, the compounds of the invention can be formulated in accordance with their use. For example, the compounds can be formulated within compositions for application to cells in tissue culture or for administration to a patient. When employed as pharmaceuticals, any of the present compounds can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids, powders, and the like. Conventional pharmaceutical carriers, aqueous, powder or oily bases, thickeners and the like may be necessary or desirable.

This invention also includes pharmaceutical compositions which contain, as the active ingredient, one or more of the compounds described herein in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material (e.g., normal saline), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. As is known in the art, the type of diluent can vary depending upon the intended route of administration. The resulting compositions can include additional agents, such as preservatives. The compounds may also be applied to a surface of a device (e.g., a catheter) or contained within a pump, patch, or other drug delivery device. The therapeutic agents of the invention can be administered alone, or in a mixture, in the presence of a pharmaceutically acceptable excipient or carrier (e.g., physiological saline). The excipient or carrier is selected on the basis of the mode and route of administration. Suitable pharmaceutical carriers, as well as pharmaceutical necessities for use in pharmaceutical formulations, are described in Remington's Pharmaceutical Sciences (E. W. Martin), a well-known reference text in this field, and in the USP/NF (United States Pharmacopeia and the National Formularly).

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The pharmaceutical compositions can be formulated so as to provide quick, sustained or delayed release of the active ingredient after administration to the patient by employing procedures known in the art.

The compositions can be formulated in a unit dosage form, each dosage containing, for example, from about 0.1 mg to about 50 mg, from about 0.1 mg to about 40 mg, from about 0.1 mg to about 20 mg, from about 0.1 mg to about 10 mg, from about 0.2 mg to about 20 mg, from about 0.3 mg to about 15 mg, from about 0.4 mg to about 10 mg, from about 0.5 mg to about 1 mg; from about 0.5 mg to about 100 mg, from about 0.5 mg to about 50 mg, from about 0.5 mg to about 30 mg, from about 0.5 mg to about 20 mg, from about 0.5 mg to about 10 mg, from about 0.5 mg to about 5 mg; from about 1 mg from to about 50 mg, from about 1 mg to about 30 mg, from about 1 mg to about 20 mg, from about 1 mg to about 10 mg, from about 1 mg to about 5 mg; from about 5 mg to about 50 mg, from about 5 mg to about 20 mg, from about 5 mg to about 10 mg; from about 10 mg to about 100 mg, from about 20 mg to about 200 mg, from about 30 mg to about 150 mg, from about 40 mg to about 100 mg, from about 50 mg to about 100 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. For preparing solid compositions such as tablets, the principal active ingredient is mixed with a pharmaceutical excipient to fount a solid preformulation composition containing a homogeneous mixture of a compound of the present invention. When referring to these preformulation compositions as homogeneous, the active ingredient is typically dispersed evenly throughout the composition so that the composition can he readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can he separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described herein and/ or known in the art. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The compositions administered to a patient can be in the form of one or more of the pharmaceutical compositions described above. These compositions can be sterilized by conventional sterilization techniques or may be sterile filtered. Aqueous solutions can be packaged for use as is, or lyophilized, the lyophilized preparation being combined with a sterile aqueous carrier prior to administration. The pH of the compound preparations typically will be between about 3 and 11, for example, between about 5 to 9, between 6 and 7, between 7 and 8. It will be understood that use of certain of the foregoing excipients, carriers, or stabilizers will result in the formation of pharmaceutical salts.

The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration.

Methods of Treatment

Chronic tissue ischemia is associated with a wide range of medical conditions that result in partial, substantially complete or complete reduction of blood flow to a body part or tissue comprising a body part and may be the result of disease, injury, or of an unknown cause, and may be influenced by one's genetic constitution. Regardless of the medical condition leading to in chronic tissue ischemia, a patient who has chronic tissue ischemia is a candidate for treatment with the pharmaceutically acceptable compositions comprising inorganic nitrite described herein. Treatment can completely or partially abolish some or all of the signs and symptoms of chronic tissue ischemia, decrease the severity of the symptoms, delay their onset, or lessen the progression or severity of subsequently developed symptoms.

New Blood Vessel Growth

As described further below, the compositions of the invention are administered for a time and in an amount sufficient to result in the growth of new blood vessels in the ischemic tissue. We may use the terms "new blood vessel growth," "new blood vessel formation" and "new blood vessel development" interchangeably. New blood vessel growth refers all phases of the process of blood vessel formation, including the initial signaling events, cellular recruitment of endothelial cells, the formation and enlargement of new vessels and connection of new vessels with pre-existing vessels. The new blood vessel growth may stem from any process that results in revascularization or neovascularization of the ischemic tissue, for example, angiogenesis, or arteriogeneis, or a combination of angiogenesis and arteriogenesis. The term vasculogenesis typically is used to describe the embryonic development of blood vessels from angioblasts. Angiogeneisis is generally understood to be a post-natal physiologic process required for would healing. Angiogenesis generally encompasses the formation of new capillaries or capillary branches by sprouting, budding and intussusception from pre-existent capillaries. Arteriogenesis i.e., the growth of preexisting arteriolar connections into true collateral arteries, is generally understood to encompass the formation of mature arteries from pre-existent interconnecting arterioles after an arterial occlusion. It shares some features with angiogenesis, but the pathways leading to it can differ, as do the final results: arteriogenesis is potentially able to fully replace an occluded artery whereas angiogenesis typically cannot. Increasing the number of capillaries within the ischemic region cannot increase blood flow when the limiting structure lies upstream of the new capillaries; formation of new collateral vessels that divert blood flow around the site of a blockage. In addition, the structures produced by angiogenesis and arteriogenesis differ in their cellular composition. Capillaries are tubes formed by endothelial cells which are supported by vascular pericytes. Arteries and veins are tubes that consist of multiple layers: the intima, which is composed of endothelial cells, pericytes, and a basement membrane; the media, which is composed principally of smooth muscle cells and their extracellular matrix; and, in the largest vessels, the adventitia, which is composed principally of fibroblasts and their extracellular matrix.

Multiple signaling pathways contribute to new blood vessel growth. At the center of these pathways is hypoxia-inducinble factor 1 (HIF-1), a heterodimeric transcription factor composed of a constitutively expressed HIF-1β subunit and an oxygen-regulated HIF-1α subunit. The HIF-1α subunit is continually synthesized and degraded within adequately perfused cells; under hypoxic conditions, the degradation of HIF-1α is inhibited, leading to its accumulation and dimerization with HIF-1β, DNA binding, recruitment of coactivators and transcriptional activation of target genes. The inbalence between oxygen supply and demand leads to hypoxia, which is a physiological stimulus that induces cells to produce angiogenic cytokines such as Vascular Endothelial Growth Factor (VEGF). These secreted proteins bind to their cognate receptors (VEGFRs) on endothelial cells and activate signal transduction pathways that stimulate cells to undergo sprouting angiogenesis. VEGF causes a massive signaling cascade in endothelial cells. Binding to VEGF receptor-2 (VEGFR-2) starts a tyrosine kinase signaling cascade that stimulates the production of factors that variously stimulate vessel permeability (eNOS, producing NO), proliferation/survival (bFGF), migration (ICAMs/VCAMs/MMPs) and finally differentiation into mature blood vessels. Other growth factors involved in new blood vessel formation include, for example, FGF which can promote proliferation and differentiation of endothelial cells, smooth muscle cells, and fibroblasts; VEGFR and NRP-1, which can integrate survival signals; Ang1 and Tie2, which can stabilize vessels; PDGF (BB-homodimer) and PDGFR, which can recruit smooth muscle cells; TGF-β, endoglin and TGF-β receptors, which can increase extracellular matrix production; MCP-1; Integrins αVβ3, αVβ5 and α5β1 which can bind matrix macromolecules and proteinases; VE-cadherin and CD31; ephrin, which can determine formation of arteries or veins; plasminogen activators, which can remodel extracellular matrix and release and activate growth factors; plasminogen activator inhibitor-1, which can stabilize blood vessels; NOS and COX-2; AC133, which can regulate angioblast differentiation; and Id1/Id3 which can regulate endothalial transdifferentiation.

In addition to their ability to activate vascular endothelial cells within the ischemic tissue, certain angiogenic cytokines, such as VEGF, PLGF and stromal-derived growth factor 1 (SDF-1), stimulate the mobilization and recruitment of a heterogeneous population of angiogenic cells from the bone marrow and other tissues to sites of angiogenesis and arteriogenesis. Cell types that can participate in these responses arc known as circulating angiogenic cells and include endothelial progenitor cells, myeloid, mesenchymal and hematopoietic progenitor cells.

Arteriogenesis seems to he triggered mainly by fluid shear stress, which is induced by the altered blood flow conditions after an arterial occlusion. Arteriogenesis involves endothelial cell activation, basal membrane degradation, leukocyte invasion, proliferation of vascular cells, neointima formation, remodeling of the extracellular matrix and cytokine participation. More specifically, mechanical stresses cause endothelial cells to produce chemical facilitators that begin the process of increasing diameter. An increase in shear stress causes an increase in the number of monocyte chemoattractant protein-1 (MCP-1) molecules expressed on the surface of vessel walls as well as increased levels of TNF-α, bFGF, and MMP. MCP-1 increases the tendency of monocytes to attach to the cell wall. TNF-α provides an inflammatory environment for the cells to develop while bFGF helps induce mitosis in the endothelial cells. Finally, MMPs remodel the space around the artery to provide room for the expansion of the new collateral artery.

Nitric oxide (NO) has been shown to positively regulate endothelial cell responses in both angiogenesis and arteriogenesis. NO increases the expression of various angiogenic factors, including VEGF, which, together with other mediators, increases NO levels via a positive feedback mechanism. In addition to stimulating the growth of nascent and immature blood vessels consisting of only fragile endothelial cells, NO recruits perivascular mural cells, which stabilize vessels and allow them to become fully functioning conduits. NO can also protect tissues against ischemic damage by slowing cellular respiration. NO has been shown to modulate several endothelial cell signaling pathways for example, Erk1/2 and PKC.

The primary enzyme responsible for NO production in the cardiovascular system is endothelial nitric oxide synthase (eNOS) which is regulated by numerous molecules and signaling pathways. Importantly, cNOS activity is also largely responsible for systemic NO production as the amount of enzyme expression is often directly proportional to NO metabolite levels. NO readily diffuses across lipid bilayers and its biological fate is dictated predominately by reactions with metalloproteins and other free radical species; the classic example being activation of the heme enzyme soluble guanylate cyclase (sGC) which initiates a signal cascade leading to vessel dilation and platelet inhibition. In addition, NO may also be oxidized through various mechanisms resulting in the formation of nitrite which can be further oxidized to nitrate ($NO_3-$).

Both nitrite and nitrate are involved in regulating production of NO from NOS independent pathways. Inorganic nitrite can undergo a one electron reduction back to NO through various mechanisms with oxygen-binding heme proteins (hemoglobin and myoglobin), deoxyhemoglobin, deoxymyoglobin, xanthine oxidoreductase, endothelial nitric oxide synthase, acidic disproportionation, and members of the mitochondrial electron transport chain, e.g., mitochondrial heme proteins all being potential electron donors. The ability of nitrite to be reduced back to NO classifies it as a unique NO donor under biological conditions, e.g., tissue ischemia, in which many of these potential reducing agents are active. NO interacts with several intracellular targets to form various NO-containing species including S-nitrosothiols, C— or N—S-nitroso compounds, and nitrosylheme adducts. Moreover, these nitroso-products may serve as a biological reservoir for NO, which can be liberated under certain conditions Administration The present methods for treating chronic tissue ischemia are carried out by administering an inorganic nitrite for a time and in an amount sufficient to result in the growth of new blood vessels in the ischemic tissue.

The amount and frequency of administration of the compositions can vary depending on, for example, what is being administered, the state of the patient, and the manner of administration. In therapeutic applications, compositions can be administered to a patient suffering from chronic tissue ischemia in an amount sufficient to relieve or least partially relieve the symptoms of chronic tissue ischemia and its complications. The dosage is likely to depend on such variables as the type and extent of progression of the chronic tissue ischemia, the severity of the chronic tissue ischemia, the age, weight and general condition of the particular patient, the relative biological efficacy of the composition selected, formulation of the excipient, the route of administration, and the judgment of the attending clinician. Effective doses can be extrapolated from dose-response curves derived from in vitro or animal model test system. An effective dose is a dose that produces a desirable clinical outcome by, for example, improving a sign or symptom of chronic tissue ischemia or slowing its progression.

The amount of inorganic nitrite per dose can vary. For example, a subject can receive from about 0.05 ug/kg to about 5000 ug/kg., e.g., about 0.05, 1, 5, 10, 25, 50, 100, 200, 250, 300, 400, 450, 500, 550, 600, 650, 700, 750, 800, 850, 900, 1000, 1250, 1500, 2000, 2500, 3000, 3500, 4000, 4500 or 5000 ug/kg. Generally, we administer nitrite in an amount such that the circulating concentration does not exceed 0.6 uM., e.g., 0.0005 uM, 0.001 uM, 0.002 uM, 0.003 uM, 0.004 uM, 0.005 uM, 0.01 uM, 0.02 uM, 0.03 uM, 0.04 uM, 0.05 uM, 0.1 uM, 0.15 uM, 0.2 uM, 0.25 uM, 0.3 uM, 0.35 uM, 0.4 uM, 0.45 uM, 0.5 uM, 0.55 uM or 0.6 uM. Thus, exemplary dosages can include 8.25 ug/kg, 16.5 ug·kg or 165 ug/kg and exemplary circulating plasma concentrations can include 0.0015 uM, 0.003 uM or 0.030 uM.

The frequency of treatment may also vary. The subject can be treated one or more times per day (e.g., once, twice, three, four or more times) or every so-many hours (e.g., about every 2, 4, 6, 8, 12, or 24 hours). The time course of treatment may be of varying duration, e.g., for two, three, four, five, six, seven, eight, nine, ten or more days. For example, the treatment can be twice a day for three days, twice a day for seven days, twice a day for ten days. Treatment cycles can be repeated at intervals, for example weekly, bimonthly or monthly, which are separated by periods in which no treatment is given. The treatment can be a single treatment or can last as long as the life span of the subject (e.g., many years).

Chronic Tissue Ischemia

Method of the invention are applicable to any of a wide range of medical conditions which have as their underlying feature a persistent reduction of or partial or complete blockage of blood flow to a tissue or organ. Thus, the methods are applicable to treatment of chronic tissue ischemia associated with a disorder, with a trauma or an environmental stress. The reduction in blood flow to a tissue can be, for example, the result of a progressive blockage of an artery due to hardening and/or loss of elasticity due to an atheromatous plaque or the presence of a clot. Reduction of blood flow to a tissue can also be the result of an environmental insult, for example, a traumatic injury or surgical procedure that interrupts the blood flow to a tissue or organ. Typically, the oxygen tension of a wound quickly and progressively decreases with the development of varying degrees of hypoxia throughout the wound region. Environmental conditions that induce hypoxia are also within the scope of the invention.

Disorders encompassed by the invention include, for example, cardiovascular disease, peripheral artery disease, arteriosclerosis, atherosclerotic cardiovascular disease, myocardial infarction, critical limb ischemic disease, stroke, acute coronary syndrome, intermittent claudication, diabetes, including type 1 and type 2 diabetes, skin ulcers, peripheral neuropathy, inflammatory bowel disease, ulcerative colitis, Crohn's disease, intestinal ischemia, and chronic mesenteric ischemia.

The methods of the invention are also applicable to chronic tissue ischemia associated with a trauma, for example, a traumatic injury such as a wound, laceration, burn, contusion, bone fracture or chronic infection. Also encompassed by the invention are tissue injuries sustained as part of any surgical procedure, for example, endarterectomy. Procedures involving tissue or organ transplantation are within the scope of the invention. Examples include vascular bypass grafts, heart, liver, lung, pancreatic islet cell transplantation as well as transplantation of tissues generated ex vivo for implantation in a host. The methods of the invention are also useful for treating a chronic ischemic condition brought about by exposure to an environmental insult, for example, chronic exposure to hypoxic conditions e.g., high altitude, or sustained aerobic exertion.

The methods provided herein are applicable to any of a wide range of tissue types including, for example, muscle, smooth muscle, skeletal muscle, cardiac muscle, neuronal tissue, skin, mesechymal tissue, connective tissue, gastrointestinal tissue or bone. Soft tissue, such as epithelial tissue, e.g., simple squamous epithelia, stratified squamous epithelia, cuboidal epithelia, or columnar epithelia, loose connective tissue (also known as areolar connective tissue), fibrous connective tissue, such as tendons, which attach muscles to bone, and ligaments, which join bones together at the joints.

The methods of the invention can include the steps of identifying a subject (e.g., a human patient) who is experiencing or is likely to experience chronic tissue ischemia. Since chronic tissue ischemia can result from a wide range of medical conditions all of which have as their underlying feature a persistent reduction of or partial or complete blockage of blood flow to a tissue, the specific signs and symptoms will vary depending upon factor or factors responsible for the reduction of blood flow.

Thus, for example symptoms of chronic tissue ischemia in peripheral artery disease (PAD), a form of peripheral vascular disease in which there is partial or total blockage of an artery, usually due to atherosclerosis in a vessel or vessels leading to a leg or arm, can include intermittent claudication, that is, fatigue, cramping, and pain in the hip, buttock, thigh, knee, shin, or upper foot during exertion that goes away with rest, claudication during rest, numbness, tingling, or coldness in the lower legs or feet, neuropathy, or defective tissue wound healing. PAD in the lower limb is often associated with diabetes, particularly type 2 diabetes. Arm artery disease is usually not due to atherosclerosis but to other conditions such as an autoimmune disease, a blood clot, radiation therapy, Raynaud's disease, repetitive motion, and trauma. Common symptoms when the aim is in motion include discomfort, heaviness, tiredness, cramping and finger pain. PAD can be diagnosed by performing one or more diagnostic tests including, for example, an ankle brachial index (ABI) test, angiography, ultrasound, or MRI analysis.

Myocardial ischemia can have few or no symptoms, although typically, it is associated with a symptoms such as angina, pain, fatigue elevated blood pressure. Diagnostic tests for myocardial ischemia include: angiography, resting, exercise, or ambulatory electrocardiograms; scintigraphic studies (radioactive heart scans); echocardiography; coronary angiography; and, rarely, positron emission tomography.

The method of the invention can also be used in conjunction with other remedies known in the art that are used to treat chronic tissue ischemia including, drug therapy, surgery, anti-inflammatory agents, antibodies, exercise, or lifestyle changes. The choice of specific treatment may vary and will depend upon the severity of the chronic tissue ischemia, the subject's general health and the judgment of the attending clinician. The present compositions can also be formulated in combination with one or more additional active ingredients, which can include any pharmaceutical agent such antihypertensives, anti-diabetic agents, statins, anti-platelet agents (clopidogrel and cilostazol), antibodies, immune suppressants, anti-inflammatory agents, antibiotics, chemotherapeutics, and the like.

EXAMPLES

Example 1

Materials and Methods

Animals and Reagents. Unless otherwise stated, male wild type (C57BL/6J) mice weighing 20-25 gm and age 2-3 months were used. The mice were bred and housed at the Association for Assessment and Accreditation of Laboratory Animal Care, International-accredited LSUHSC-Shreveport animal resource facility and maintained according to the National Research Council's Guide for Care and Use of Laboratory Animals. All experimental protocols were approved by the LSU Institutional Animal Care and Use Committee. Sodium nitrite, sodium nitrate, phosphate buffered saline (PBS), and all other chemicals were purchased from Sigma Chemical (St. Louis, Mo.). Hind-Limb Ischemia Model. Hind limb ischemia was induced by ligating the left common femoral artery proximal to origin of profunda femoris artery according to Senthilkumar, A., Smith, R. D., Khitha, J., Arora, N., Veerareddy, S., Langston, W., Chidlow, J. H., Jr., Barlow, S. C., Teng, X., Patel, R. P., et al. 2007. Arterioscler Thromb Vasc Biol 27:1947-1954. Mice were anesthetized with intraperitoneal injection of ketamine (100 mg/kg) and xylazine (8 mg/kg); surgery was performed unused aseptic conditions. The common femoral vein and femoral nerve were dissected away from the artery. Two ligatures were placed in the common femoral artery proximal to the profunda femoris artery and then transected between the two ligations. The incision was then closed and the ligation was immediately verified by laser Doppler measurement of tissue blood flow.

Vascular casting. Hind limb vascular casting of ischemic limbs was performed using Microfil silicone injection MV120. Before vascular casting, papaverine (5 ng/ml) and adenosine (1 mg/ml) were given intravenously to increase perfusion of the casting resin. Briefly, the abdominal aorta proximal to the femoral artery bifurcation was ligated with 5.0 silk suture material and cannulated caudal to the ligation using PE50 tubing held in place with a silk ligature. 400 µl of Microfil was infused into the aortic catheter and allowed to set in situ for 16 hours at 4° C. Hind limb muscle tissue was cleared by incubating tissues in graded glycerol solutions of 40%, 60%, 80%, and 100% for 24 hours each. Vascular casts were subsequently photographed using a stereomicroscope.

Laser Doppler measurements of tissue blood flow. The Vasamedics Laserflo BPM2 deep tissue penetrating laser doppler device was used to measure hind limb blood flow. The tip of laser probe was placed with stable positioning using a probe stand over the medial calf muscle of mice. Readings were recorded in ml of blood flow per 100 g tissue per minute from non-ischemic and ischemic limbs. Daily blood flow measurements were taken before the first nitrite or nitrate injection of a 24 hour period in order to obtain representative steady state changes in perfusion. Percent change in tissue blood flow was determined by dividing ischemic limb blood flow by non-ischemic limb blood flow and multiplied by 100. In a separate series of experiments, blood flow was also measured within 30 seconds after nitrite or nitrate administration to assess acute changes in blood flow.

Vascular density measurement. Determination of the vascular density of muscle tissue was performed as described in Senthilkumar, A., Smith, R. D., Khitha, J., Arora, N., Veerareddy, S., Langston, W., Chidlow, J. H., Jr., Barlow, S. C., Teng, X., Patel, R. P., et al, 2007. Arterioscler Thromb Vasc Biol 27:1947-1954. Briefly, ischemic (left) and non-ischemic (right) tissues were dissected and embedded in OCT freezing medium and frozen and 3 micron sections cut. Slides were fixed at −20° C. in 95% ethanol/5% glacial acetic acid for one hour. Slides were blocked overnight with 5% horse serum in PBS at 4° C. Anti-CD31 (PECAM-1) was added at 1:200 dilution (in PBS with 0.05% horse serum) and incubated at 37° C. for one hour. Slides were washed 3 times with 1% horse serum/PBS and Cy3 conjugated anti-rat secondary antibody was added at 1:250 dilution (in PBS with 0.05% horse serum) and incubated at room temperature for one hour. Slides were washed and mounted using Vectashield DAPI (4',6-Diamidine-2'-phenylindole dihydrochloride) nuclear counterstain. At least 4 fields were acquired per section with 4 sections stained per muscle specimen. Pictures were taken with a Hamamatsu digital camera using a Nikon TE-2000 epifluorescent microscope (Nikon Corporation, Japan) with TRITC and DAPI illumination at 200× magnification for CD31 and DAPI staining, respectively. Simple PCI software version 6.5 (Compix Inc, Sewickly, Pa.) was used to quantitate the surface area of CD31 and DAPI staining per section. Vascular density was measured as the ratio between CD31 pixel density divided by DAPI pixel density. Image acquisition and vascular density measurements were accumulated, analyzed, and calculated in a double blinded fashion before identity of the data were used for statistical analysis and graph generation.

Measurement of Nitrite, NO Metabolite, Tissue cGMP, and eNOS Protein Levels. Nitrite and tissue NO metabolite levels tissue (nitrosothiol, C- or N-nitroso compounds, or iron-nitrosyl proteins which are collectively referred to SNO+XNO) whether were measured using chemiluminescence techniques according to Lang, J. D., Jr., Teng, X., Chumley, P., Crawford, J. H., Isbell, T. S., Chacko, B. K., Liu, Y., Jhala, N., Crowe, D. R., Smith, A. B., et al. 2007. *J Clin Invest.* 117:2583-2591. Gastrocnemius muscle tissue cGMP levels were determined using the cGMP ELISA from Cayman Chemical (Ann Arbor, Mich.) according to the manufacturer's directions. Specimens were collected within 2 min after injection of either PBS or sodium nitrite. Total eNOS protein levels in hind-limb tissue were determined by Western blot analysis.

Statistical analysis. Blood flow, vascular density, endothelial cell proliferation, tissue nitrate and NO metabolites, and cGMP data were analyzed using Students T-test (unpaired) between sodium nitrite or sodium nitrate vs. PBS control groups with a minimum of P<0.05 necessary for significance. Blood nitrite measurements and acute changes in blood flow from experimental groups were compared against PBS controls and day 0 time points, respectively, using one-way ANOVA with Bonferroni's post-test with a minimum of p<0.05 necessary for significance. Statistics were done with GraphPad Prism 4.0 software. The number of mice used per reported experiment is designated in the Examples below.

Example 2

Chronic Sodium Nitrite Therapy Increased Ischemic Tissue Blood Flow

Figures 2A, 2B:
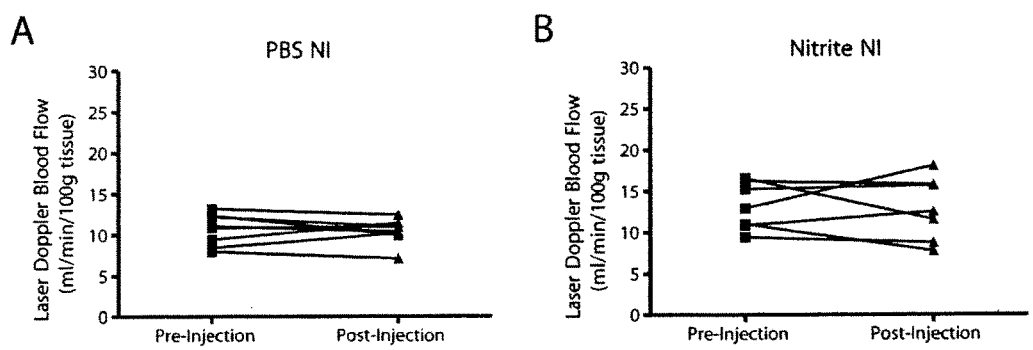
FIGS. 2A and 2B depict the results of an analysis demonstrating that chronic sodium nitrite treatment did not alter non-ischemic hind-limb blood flow.

We examined the effect of a range of sodium nitrite doses on ischemic tissue blood flow in the mouse hind-limb ischemia model described in Example 1. Sodium nitrite was administered via intraperitoneal injection twice a day in a dose range of 8.25-3,300 µg/kg; 15 mice were used per treatment group. Blood flow was measured according the laser Doppler method of Example 1. Changes in ischemic tissue perfusion were determined by measuring ischemic limb blood flow which was divided by the respective contralateral non-ischemic limb blood flow to calculate a percent change for each animal. As shown in FIG. 1A, nitrite doses of 8.25, 16.5, 165, and 3,300 µg/kg all increased the percentage blood flow in ischemic hind limbs by day 3 post ligation which progressively increased by day 7. The 165 µg/kg sodium nitrite dose revealed optimal temporal efficacy compared to higher and lower doses. We next examined whether sodium nitrite increased ischemic tissue blood flow through a nitric oxide (NO) dependent mechanism. As shown in FIG. 1B, the NO scavenger, carboxy PTIO (2-(4-Carboxyphenyl)-4,4,5,5-tetramethylimidazoline-1-oxyl-3-oxide) at a dose of 1 mg/kg daily, significantly attenuated the ability of sodium nitrite to restore ischemic limb blood flow. Injection of 165 µg/kg sodium nitrite enhanced blood flow in hind limbs that were ischemic for 24 h, as shown in FIG. 1C; no changes in bloof flow were observed in hind limbs that were ischemic for 24 h that were injected with PBS injection (FIG. 1D). Importantly, neither PBS nor sodium nitrite altered hind limb blood flow in the nonischemic limbs as shown in FIGS. 2A and 2B, respectively; 10 mice were used per treatment group. As shown in FIG. 3, when sodium nitrate was used instead of sodium nitrite, the lowest dose of sodium nitrate (8.25 µg/kg) augmented ischemic limb blood flow by days 5 and 7.

Example 3

Figure 4A:
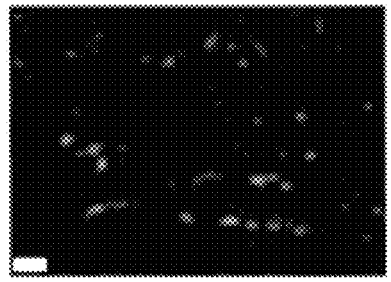
FIGS. 4A, 4B, 4C, 4D, 4E and 4F depict the results of an analysis demonstrating that chronic sodium nitrite treatment increased ischemic tissue vascular density in an NO-dependent manner.
Figure 4B:
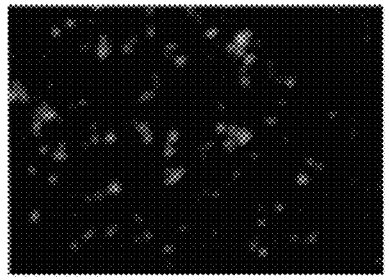
Figure 4C:
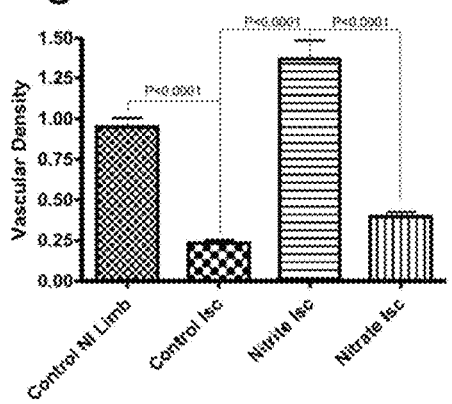
Figure 4D:
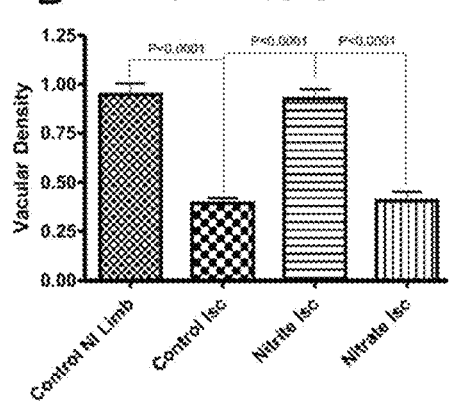
Figure 4E:
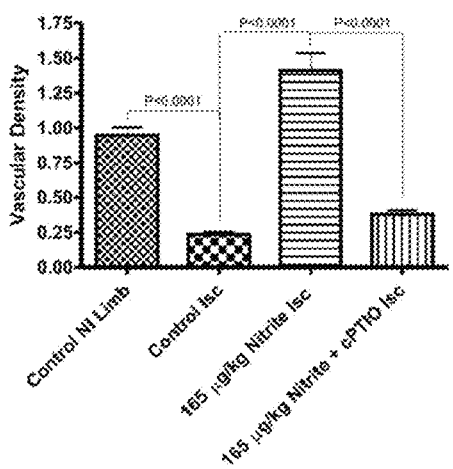
Figure 4F:
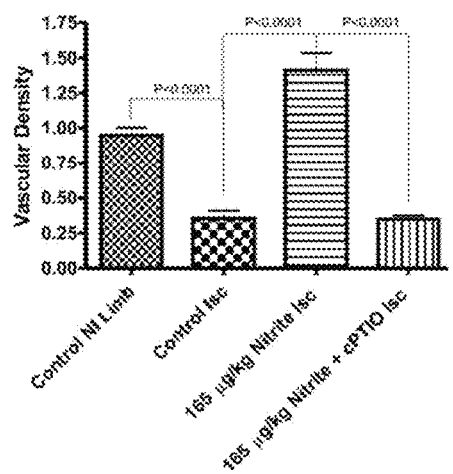
Figure 5A:
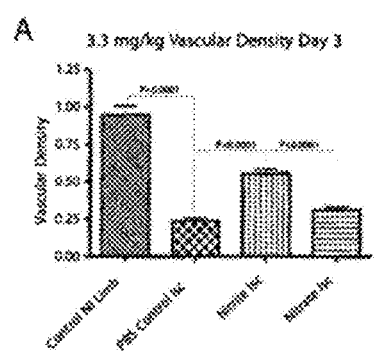
FIGS. 5A, 5B and 5C depict the results of an analysis of vascular density measurements from high-dose sodium nitrite and non-ischemic nitrite tissues.
Figure 5B:
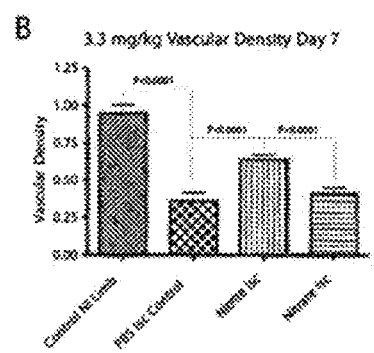
Figure 5C:
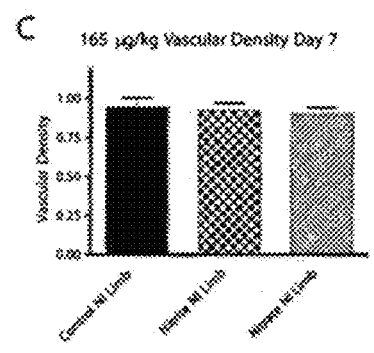

Chronic Sodium Nitrite Therapy Selectively Increased Ischemia-Induced Angiogenesis We next examined the effect of chronic sodium nitrite therapy on ischemic tissue vascular density. Vascular density was measured according to the method of Example 1. FIGS. 4A and 4B illustrate endothelial cell CD31 staining in red with DAPI nuclear counterstaining in blue of ischemic gastrocnemius muscle at day 7 from animals treated with sodium nitrate or sodium nitrite (165 µg/kg), respectively. Endothelial staining of CD31 was much more abundant in ischemic muscle tissue in mice receiving sodium nitrite as compared to PBS or sodium nitrate controls. Quantitative analysis of vascular density revealed that sodium nitrite (165 µg/kg) therapy significantly increased vascular density at days 3 and 7 compared to PBS or sodium nitrate control treatments (FIGS. 4C and 4D); 10 mice were used per treatment group. Consistent with changes in tissue blood flow, cPTIO cotreatment prevented nitrite augmentation of angiogenesis in the ischemic hind limbs at days 3 and 7 (FIGS. 4E and 4F). High-dose sodium nitrite (3,300 µg/kg) was less potent in augmenting ischemic tissue vascular density compared to low-dose (165 µg/kg) nitrite, consistent with observations of percentage blood flow changes in ischemic tissues (FIGS. 5A and 5B). Importantly, sodium nitrite did not significantly alter nonischemic tissue vascular density, highlighting the site-specific activity of chronic nitrite therapy (FIG. 5C); 10 mice were used in each group.

Example 4

Chronic Sodium Nitrite Therapy Increased Ischemic Endothelial Cell Proliferation The effect of sodium nitrite on endothelial cell proliferation in ischemic gastrocnemicus tissues was analyzed in the hind-limb ischemia model of Example 1. FIGS. 6A and 6B illustrate the amount of endothelial cell proliferation as determined by Ki67 staining (green) of ischemic tissues along with endothelial cell CD31 labeling (red) and DAPI nuclear staining (blue) from day 3 sodium nitrate or nitrite (165 µg/kg) treatments, respectively. FIG. 6C quantifies the amount of Ki67 colocalization with DAPI nuclear counter stain at day 3 for sodium nitrite or nitrate, and demonstrated that sodium nitrite significantly increased Ki67 nuclear localization in ischemic but not non-ischemic tissues and that the increase in KI67 nuclear localization was blocked by carboxy PTIO. Moreover, sodium nitrite significantly increased Ki67 to CD31 colocalization in ischemic tissues and this increase in colocalization was blocked by cPTIO (FIG. 6D); 10 mice were used per treatment group.

Example 5

Effect of Chronic Nitrite Administration on Blood and Tissue Nitrite Levels

Figures 7A, 7B, 7C, 7D, 7E:
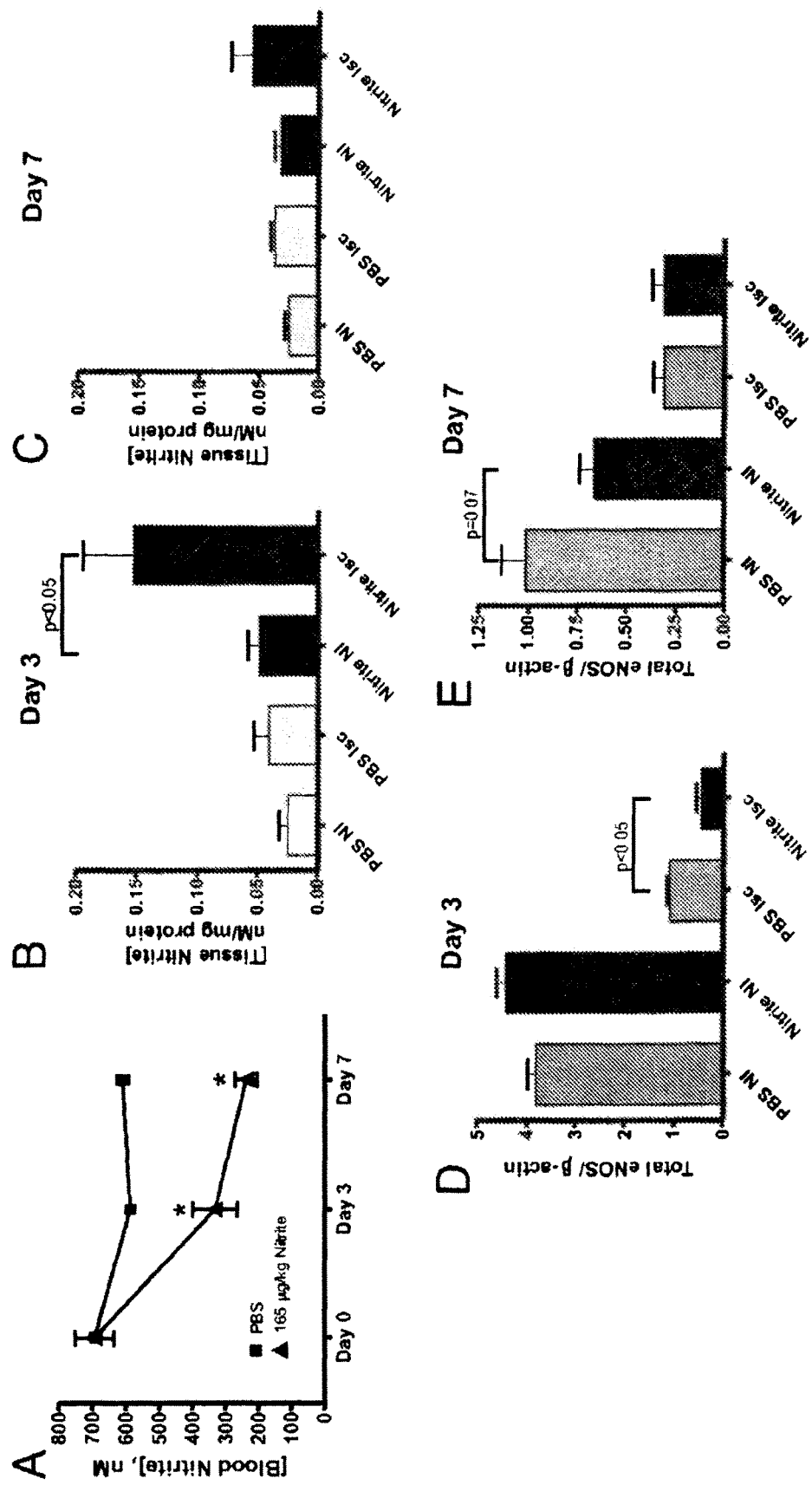
FIGS. 7A, 7B, 7C, 7D and 7E depict the results of an experiment demonstrating that chronic sodium nitrite treatment altered blood and tissue nitrite levels.

Analysis of blood and tissue nitrite levels in nitrate-treated and control animals was performed according to the method in Example 1. As shown in FIG. 7A blood levels of nitrite significantly decreased over time in the 165-µg/kg sodium nitrite therapy and were minimally altered with PBS treatment. FIGS. 7B and 7C show tissue nitrite levels at day 3 and day 7, respectively, of nitrite treatment; 10 mice were used per treatment group. Nitrite therapy significantly increased levels of tissue nitrite in ischemic but not nonischemic tissue nitrite at day 3 (FIG. 7B). At day 7 tissue nitrite levels did not differ significantly between nitrite-treated animals and PBS treated control animals (FIG. 7C). Together, these data demonstrated that chronic sodium nitrite therapy resulted in preferential early tissue accumulation of nitrite in ischemic versus nonischemic tissues. The decreased blood nitrite levels in response to chronic sodium nitrite therapy prompted us to examine total eNOS protein levels in hind-limb muscle tissue from PBS or 165 µg/kg sodium nitrite therapy. FIG. 7D shows that at day 3, chronic sodium nitrite therapy significantly decreased eNOS protein expression in ischemic hind-limb tissue without altering expression in nonischemic hind-limb tissue. At day 7, as shown in FIG. 7E, sodium nitrite reduced of eNOS protein expression in nonischemic tissue with no effect on ischemic tissue; 3 mice were used per experimental group for the experiment show in FIG. 7. These data suggested that the decrease in blood nitrite levels could be due to decreased eNOS protein expression in response to chronic sodium nitrite therapy.

Example 6

NO Tissue Metabolites and Tissue cGMP During Chronic Sodium Nitrite Therapy

Figures 8A, 8B, 8C, 8D:
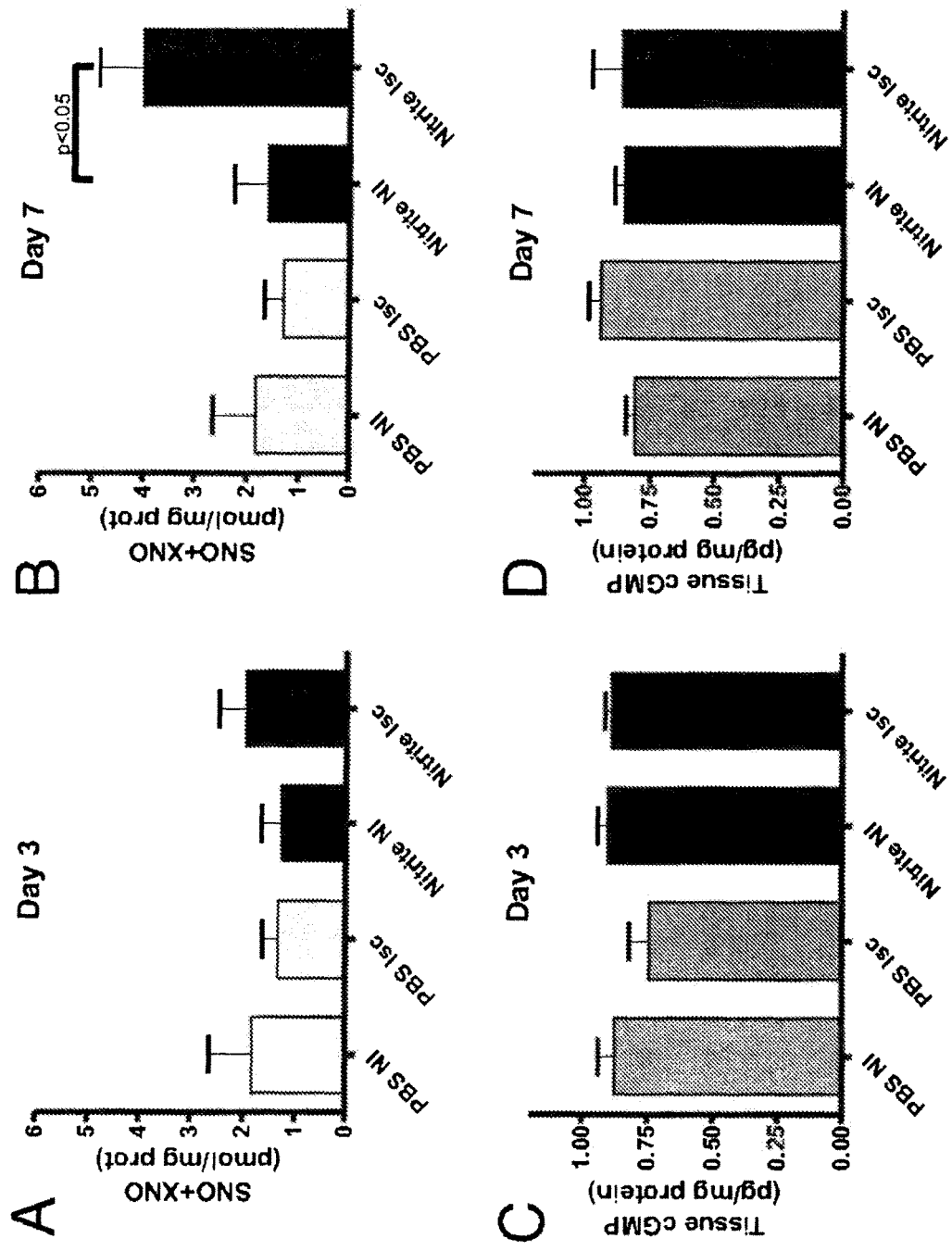
FIGS. 8A, 8B, 8C and 8D depict the results of an experiment analyzing the effect of chronic sodium nitrite treatment on tissue NO metabolites and cGMP levels.

The effect of nitrite treatment on levels of the NO metabolites, SNO and XNO was measure according to the method in Example 1. Twenty mice were used per treatment group. Tissue SNO+XNO levels for 165 µg/kg sodium nitrite-treated animals or PBS-treated controls at day 3 and 7 are shown in FIGS. 8A and 8B, respectively Neither sodium nitrite (165 µg/kg) nor PBS significantly altered tissue SNO+XNO levels at day 3. However, nitrite therapy significantly increased SNO+XNO levels in ischemic tissue at day 7 compared to PBS. These data revealed a delayed effect of nitrite therapy on tissue nitrosothiol, C-/N-nitroso compounds, and iron-nitrosyl proteins and demonstrated preferential production of NO containing intermediates in ischemic tissues.

We also examined whether chronic sodium nitrite therapy selectively increased cGMP levels in nitrite-treated animals. As shown in FIGS. 8C and 8D, neither 165 µg/kg sodium nitrite nor PBS significantly altered tissue cGMP levels at either day 3 or 7, respectively.

Example 7

Chronic Sodium Nitrite Therapy Augmented Arteriogenesis and Acute Changes in Ischemic Tissue Blood Flow Stimulation of angiogenesis alone during chronic ischemia is generally insufficient for restoring tissue perfusion.

Figures 9A, 9B, 9C, 9D, 9E:
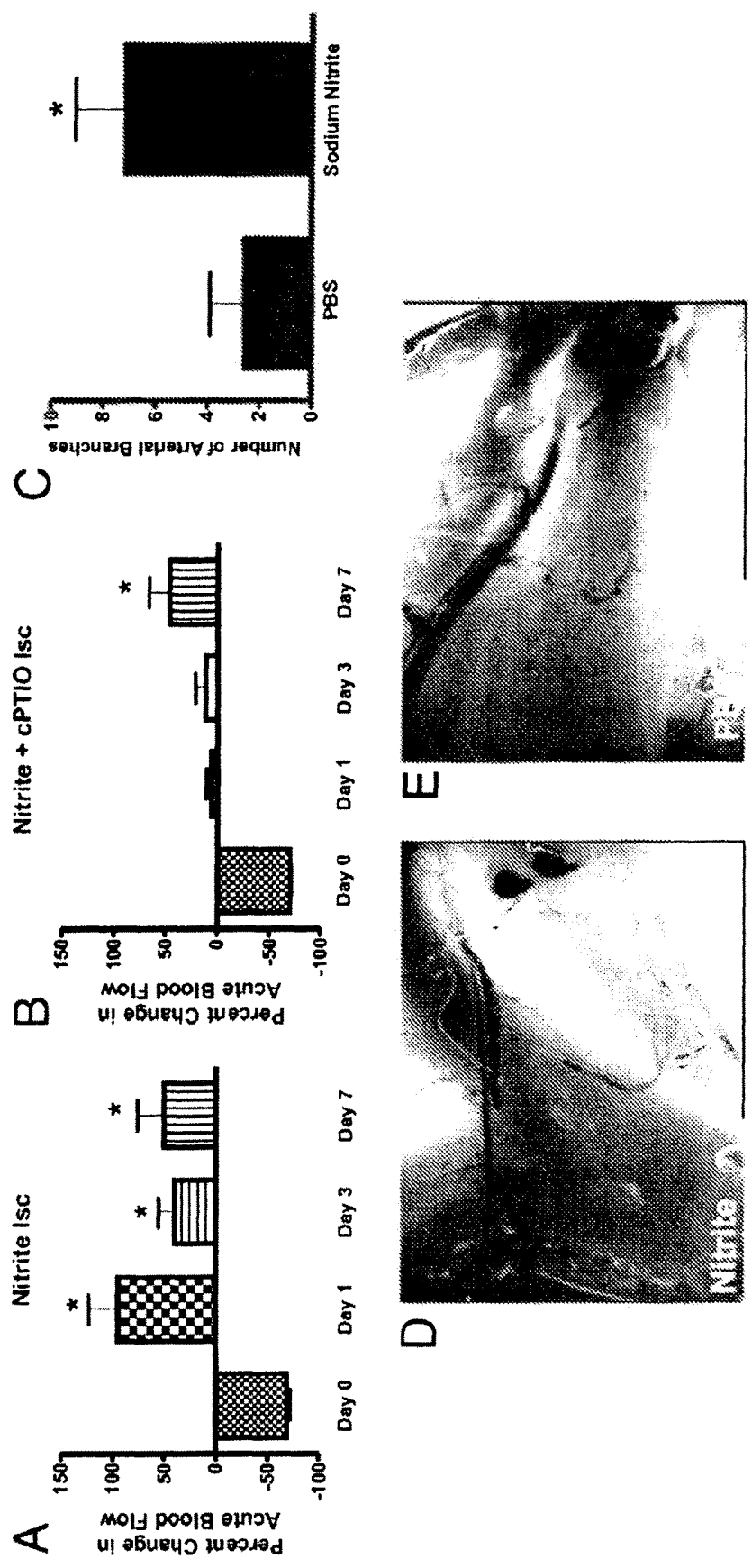
FIGS. 9A, 9B, 9C, 9D and 9E depict the results of an experiment demonstrating that chronic sodium nitrite treatment acutely increased ischemic tissue blood flow and stimulates arteriogenesis.

Increased arteriogenesis through the recruitment and differentiation of smaller arterioles is important to supply newly formed microvasculature. Moreover, an acute increase in vascular shear stress due to increased blood flow is a critical mediator of arteriogenesis. We examined the effect of 165 μg/kg sodium nitrite on acute changes (30 sec) in ischemic and nonischemic tissue perfusion according to the method in Example 1. Ten mice were used per treatment group. As shown in FIG. 9A, 165 μg/kg sodium nitrite significantly enhanced ischemic tissue blood flow by 92.3±18% within 30 sec of administration at day 1 after ligation. The duration of increased blood flow after sodium nitrite injection persisted >10 min (data not shown). The ability of nitrite to induce large increases in acute blood flow was inversely proportional to the duration of tissue ischemia, because animals receiving chronic nitrite therapy showed a lesser, yet still significant, increase in acute blood flow change at days 3 and 7. This observation could be because significant angiogenic activity had occurred, thereby diminishing the degree of tissue ischemia. The sodium nitrite-dependent changes in acute tissue blood flow involved NO, because, as shown in FIG. 9B, cPTIO significantly blunted this response at early time points.

To further evaluate arteriogenesis activity, we performed hind-limb ligations distal to the profunda femoris and proximal to the knee to more easily distinguish changes in the arterial supply. As shown in FIG. 9C, the number of arterial branch points was significantly greater in tissues from sodium nitrite-treated animals that in corresponding tissues from PBS-treated control animals. Arterial casts were made according to the method in Example 1. FIG. 9D shows a representative example of an arterial cast from a sodium nitrite-treated ischemic limb at day 7; FIG. 9E shows an arterial cast of a PBS-treated ischemic limb at day 7. Numerous collateral vessels could be observed throughout the tissue in response to nitrite therapy, indicating enhanced arteriogenesis. Conversely, PBS treatment did not enhance arterial perfusion, and minimal collateral vessels are observed. Together, these data demonstrate that chronic nitrite therapy augmented arteriogenesis activity in ischemic tissue.

Example 8

Figure 10:
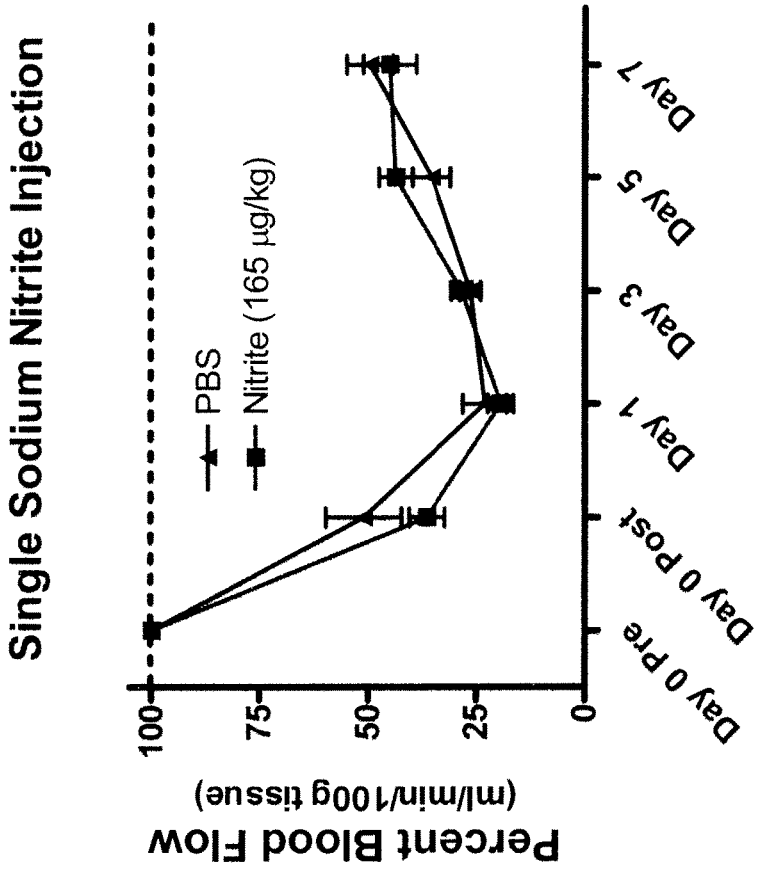
FIG. 10 depicts the results of an experiment demonstrating that single bolus I.P. injection of sodium nitrite did not restore ischemic hind-limb blood flow.

Effect of Single Bolus I.P. Injection of Sodium Nitrite on Ischemic Hind Limb Blood Flow Permanent femoral artery ligation was performed on the left hind limb of C57BL/6J mice (n=3 per treatment group) according to the method in Example 1. A single bolus injection of either PBS or sodium nitrite (165 μg/kg) was given I.P. 45 minutes after completing the ligation. Blood flow recovery was monitored every other day over a 7 day period to evaluate the efficacy of single bolus injection therapy. As shown in FIG. 10, a single bolus I.P. injection of sodium nitrite did not restore ischemic hind limb blood flow. "Day 0 Pre" on the x-axis refers to blood flow on the day of ligation before the ligation was performed; "Day 0 Post" on the x-axis refers to blood flow on the day of ligation after the ligation was performed.

Example 9

Effect of Delayed Sodium Nitrite Therapy on Ischemic Hind Limb Blood Flow

Figure 11:
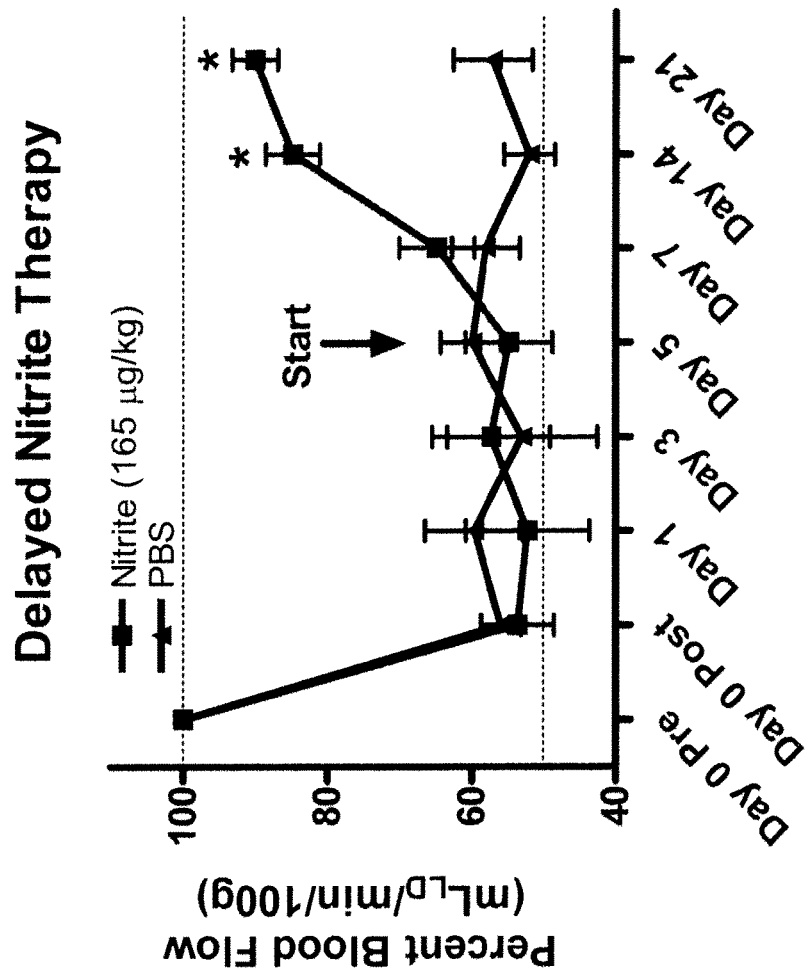
FIG. 11 depicts the results of an experiment demonstrating that delayed nitrite treatment restored ischemic hind-limb blood flow. *$p<0.01$ sodium nitrite versus PBS at each respective time point.

We also evaluated the effect of delaying chronic sodium nitrite treatment on restoration of hind limb blood flow. Permanent femoral artery ligation was performed on the left hind limb of C57BL/6J mice (n=6 per treatment group) as described in Example 1. PBS or sodium nitrite (165 μg/kg) I.P. injections (b.i.d.) were started the morning of day 5 post-ligation and continued daily throughout the remainder of the study. Blood flow recovery was monitored throughout the study using deep tissue penetrating laser Doppler as described in Example 1. As shown in FIG. 11, delayed nitrite therapy restored ischemic hind limb blood flow. "Day 0 Pre" on the x-axis refers to blood flow on the day of ligation before the ligation was performed; "Day 0 Post" on the x-axis refers to blood flow on the day of ligation after the ligation was performed.

Example 10

Figure 13:
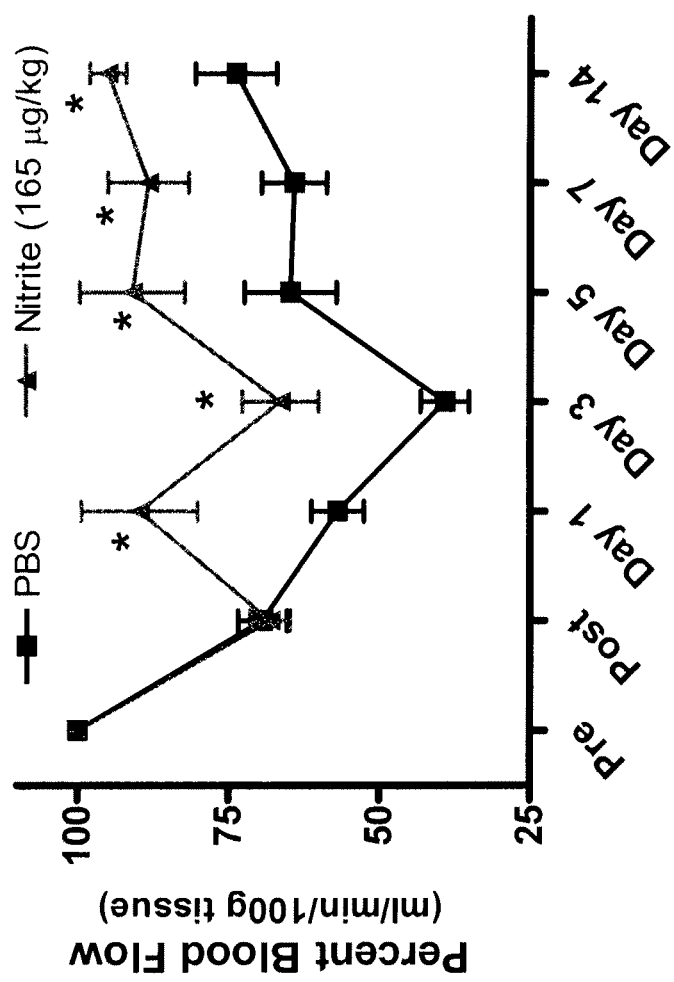
FIG. 13 depicts the results of an experiment demonstrating that sodium nitrite restored Db/Db diabetic mouse ischemic hind-limb blood flow. (*$p<0.01$ sodium nitrite versus PBS at each respective time point.)

Sodium Nitrite Treatment Restored Ischemic Hind-Limb Blood Flow in Diabetic Mice We evaluated the effect of sodium nitrite treatment on ischemic hind limb blood flow in a diabetic mouse model. Permanent femoral artery ligation was performed on the left hind limb of Db/Db diabetic mice (n=5 per treatment group) according to the methods in Examples 1 and 2, except that the mice were anesthetized with 2% inhaled isofluorane. PBS or sodium nitrite (165 μg/kg) I.P. injections (b.i.d.) were started post-ligation and continued daily throughout the remainder of the study. Blood flow recovery was monitored throughout the study using deep tissue penetrating laser Doppler according to the method in Example 1. As shown in FIG. 13, sodium nitrite treatment restored ischemic hind-limb blood flow in diabetic mice. Blood flow in the ischemic-hind limbs of the nitrite-treated animals was significantly greater than that of the PBS-treated control animals at all time points analyzed and approached preligation levels by the end of the study.

Example 11

Continuous Sodium Nitrite Therapy Enhanced Excision Wound Healing

Figure 12:
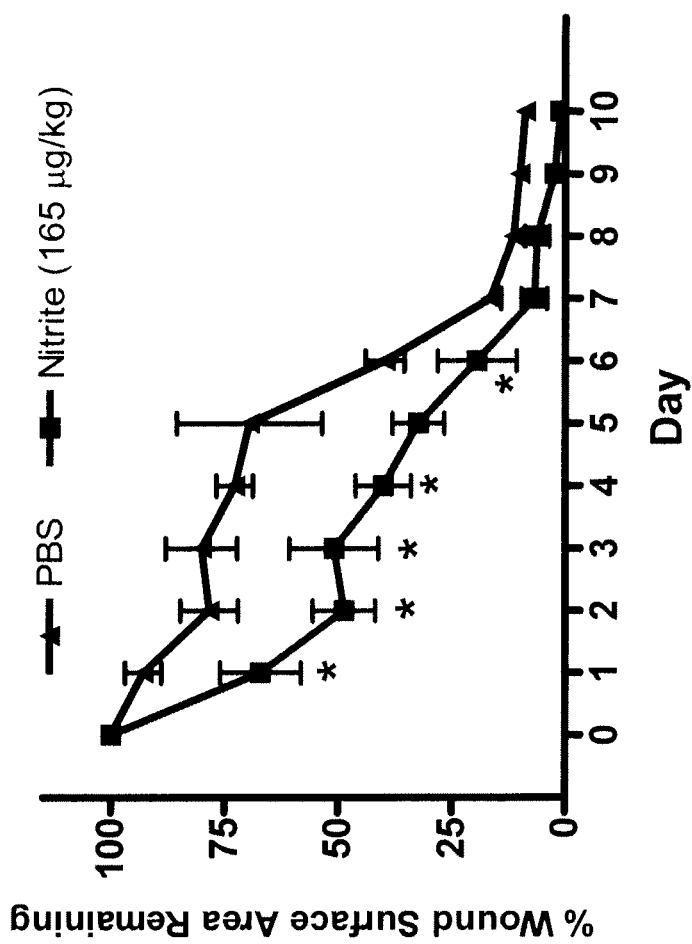
FIG. 12 depicts the results of an experiment demonstrating that continuous nitrite treatment enhanced wound healing. (*$p<0.01$ sodium nitrite versus PBS at each respective time point.)

Full thickness excisional wounds were created using a 4 mm punch biopsy device. C57BL/6J mice were anesthetized according to the method in Example 1. Wounds were created by pinching the loose skin and punching a half circle biopsy to obtain a uniform 4 mm diameter wound (n=4 per treatment group). PBS or sodium nitrite (165 μg/kg) I.P. injections (b.i.d.) were began immediately after wounding and continued daily throughout the remainder of the study. Wound diameter was measured using digital calipers and plotted as the percent wound surface area remaining at each successive day. As shown in FIG. 12, continuous sodium nitrite therapy enhanced excision wound healing. The percent wound surface remaining was significantly less in the sodium nitrite-treated animals than in the PBS-treated control animals for the first six days of the study, and remained, lower for the remaining four days.

A number of embodiments of the invention have been described. Nevertheless, it will be understood that various modifications may be made without departing from the spirit and scope of the invention. Accordingly, other embodiments are within the scope of the following claims.

What is claimed is:

1. A method of treating peripheral neuropathy in a human subject, the method comprising: orally administering to the subject a pharmaceutical composition comprising about 5 mg to about 50 mg of sodium nitrite one to six times per day for at least ten days, thereby treating the peripheral neuropathy.

2. The method of claim 1, further comprising a step of ceasing the administration of the pharmaceutical composition when a symptom of peripheral neuropathy in the subject improves.

3. The method of claim 2, wherein the sodium nitrite is administered to a circulating nitrite concentration in the subject of about 0.01 M to about 0.6 M.

4. The method of claim 2, wherein the method stimulates blood vessel growth in ischemic tissue but not in non-ischemic tissue.

5. The method of claim 4, wherein the ischemic tissue comprises skeletal muscle, smooth muscle, cardiac muscle, neuronal tissue, skin, mesenchymal tissue, connective tissue, gastrointestinal tissue or bone.

6. The method of claim 5, wherein administration of said sodium nitrite alters nitrite levels in the blood.

7. The method of claim 5, wherein administration of said sodium nitrite raises nitrite levels in the ischemic tissue.

8. The method of claim 1, wherein the sodium nitrite is administered two times per day.

\* \* \* \* \*